United States Patent [19]

Nunes et al.

[11] Patent Number: 5,776,931
[45] Date of Patent: Jul. 7, 1998

[54] NAPHTHIMIDAZOLYL NEUROPEPTIDE Y RECEPTOR ANTAGONISTS

[75] Inventors: Anne Marie Nunes, Andover, Mass.; Hamideh Zarrinmayeh, Carmel, Ind.

[73] Assignee: Eli Lilly and Company, Indianapolis, Ind.

[21] Appl. No.: 775,533

[22] Filed: Jan. 9, 1997

[51] Int. Cl.$^6$ .............. A61K 31/535; A61K 31/445; A61K 31/415; C09D 413/00; C09D 421/00; C09D 235/02

[52] U.S. Cl. .............. 514/232.8; 514/322; 514/393; 514/394; 514/395; 544/139; 546/199; 548/302.1

[58] Field of Search .................. 514/322, 232.8, 514/393, 394, 395; 548/302.1; 544/139; 546/199

[56] References Cited

U.S. PATENT DOCUMENTS 4,623,379  11/1986  Baum et al. .................. 71/92

*Primary Examiner*—William R. A. Jarvis
*Attorney, Agent, or Firm*—Paul J. Gaylo; David E. Boone

[57] ABSTRACT

This invention provides a series of substituted 1H-naphth[2,3-d]imidazoles which are useful in treating a condition associated with an excess of neuropeptide Y. This invention also provides methods employing these substituted 1H-naphth[2,3-d]imidazoles as well as pharmaceutical formulations with comprise as an active ingredient one or more of these compounds.

30 Claims, No Drawings

NAPHTHIMIDAZOLYL NEUROPEPTIDE Y RECEPTOR ANTAGONISTS

BACKGROUND OF THE INVENTION

Neuropeptide Y is a peptide present in the central and peripheral nervous systems. The peptide co-exists with noradrenaline in many neurons and acts as a neurotransmitter per se or synergistically together with noradrenaline. Neuropeptide Y-containing fibers are numerous around arteries in the heart, but are also found around the arteries in the respiratory tract, the gastrointestinal tract, and the genitourinary tract. Neuropeptide Y is also present in the cerebrum with effects on blood pressure, feeding, and the release of different hormones. Alterations in central concentrations of neuropeptide Y have been implicated in the etiology of psychiatric disorders.

Neuropeptide Y was discovered, isolated and sequenced in 1982 from porcine brain as part of a general screening protocol to discover carboxy-terminal amidated peptides and was named neuropeptide Y due to its isolation from neural tissue and the presence of tyrosine as both the amino and carboxy terminal amino acid. Neuropeptide Y is a member of the pancreatic family of peptides and shares significant sequence homology with pancreatic polypeptide and peptide YY.

Neuropeptide Y and the other members of its family of peptides all feature a tertiary structure consisting of an N-terminal polyproline helix and an amphiphilic α-helix, connected with a β-turn, creating a hairpin-like loop, which is sometimes referred to as the pancreatic polypeptide (PP) fold. The helices are kept together by hydrophobic interactions. The amidated C-terminal end projects away from the hairpin loop.

Subsequent to its discovery neuropeptide Y was identified as being the most abundant peptide in the central nervous system with widespread distribution including the cortex, brainstem, hippocampus, hypotahlamus, amygdala, and thalamus as well as being present in the peripheral nervous system in sympathetic neurons and adrenal chromaffin cells.

Neuropeptide Y seems to fulfill the main criteria for a role as a neurotransmitter, as it is stored in synaptic granules, is released upon electrical nerve stimulation, and acts at specific receptors. It is clear that neuropeptide Y is an important messenger in its own right, probably in the brain, where neuropeptide Y potently inhibits the activity of adenylate cyclase and induces an increase in the intracellular levels of calcium. Central injection of neuropeptide Y results in blood pressure changes, increased feeding, increased fat storage, elevated blood sugar and insulin, decreased locomotor activity, reduced body temperature, and catalepsy.

Neuropeptide Y (as well as its chemical relatives) acts upon membrane receptors that are dependent on guanyl-nucleotide binding proteins, known as G protein-coupled receptors. G proteins are a family of membrane proteins that become activated only after binding guanosine triphosphate. Activated G proteins in turn activate an amplifier enzyme on the inner face of a membrane; the enzyme then converts precursor molecules into second messengers.

Neuropeptide Y appears to interact with a family of closely related receptors. These receptors are generally classified into several subtypes based upon the ability of different tissues and receptors to bind different fragments of neuropeptide Y and other members of the PP family of peptides. The Y1 receptor subtype appears to be the major vascular neuropeptide Y receptor. The Y2 receptor subtypes can also occur postjunctionally on vascular smooth muscle.

The as-yet-unisolated Y3 receptor subtype appears to be neuropeptide Y-specific, not binding peptide YY. This receptor is likely to be present in the adrenal tissues, medulla, heart, and brain stem, among other areas. [For a review of neuropeptide Y and neuropeptide Y receptors, see, e.g., C. Wahlestedt and D. Reis, *Annual Review of Pharmacology and Toxicology*, 33:309–352 (1993); D. Gehlert and P. Hipskind, *Current Pharmaceutical Design*, 1:295–304 (1995)].

In view of the wide number of clinical maladies associated with an excess of neuropeptide Y, the development of neuropeptide Y receptor antagonists will serve to control these clinical conditions. The earliest such receptor antagonists, such as Patent Cooperation Treaty Patent Publication WO 91/08223, published Jun. 13, 1991, and Patent Cooperation Treaty Patent Publication WO 94/00486, published Jan. 6, 1994, were peptide derivatives. These antagonists are of limited pharmaceutical utility because of their metabolic instability.

This invention provides a class of potent non-peptide neuropeptide Y receptor antagonists. By virtue of their non-peptide nature, the compounds of the present invention do not suffer from the shortcomings, in terms of metabolic instability, of known peptide-based neuropeptide Y receptor antagonists.

SUMMARY OF THE INVENTION

This invention encompasses methods for the treatment or prevention of a physiological disorder associated with an excess of neuropeptide Y, which method comprises administering to a mammal in need of said treatment an effective amount of a compound of Formula I

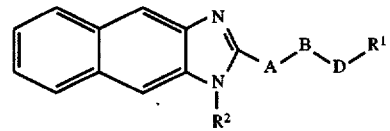

wherein

A is a bond or $C_1$–$C_6$ alkylenyl;

B is a bond, —O—, —NH—, or —S—;

D is a bond or $C_1$–$C_6$ alkylenyl;

$R^1$ is $C_3$–$C_8$ cycloalkyl, $C_3$–$C_8$ cycloalkenyl, phenyl, phenoxy, naphthyl, or naphthyloxy,
  any one of which phenyl, $C_3$–$C_8$ cycloalkyl, phenoxy, naphthyl, or naphthyloxy moieties may be substituted with one or more moieties selected from the group consisting of halo, trifluoromethyl, $C_1$–$C_6$ alkyl, $C_2$–$C_7$ alkenyl, $C_2$–$C_7$ alkynyl, $C_1$–$C_6$ alkoxy, $C_1$–$C_6$ alkylthio, $C_1$–$C_6$ alkylamino, $C_2$–$C_7$ alkanoyl, hydroxy, heterocyclic, unsaturated heterocyclic, $C_3$–$C_8$ cycloalkyl, $C_3$–$C_8$ cycloalkenyl, phenyl, phenoxy, benzyl, benzyloxy, and benzoyl;

$R^2$ is $C_1$–$C_{12}$ alkyl, $C_2$–$C_7$ alkenyl, $C_2$–$C_7$ alkynyl, heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)-, which $C_1$–$C_{12}$ alkyl, $C_2$–$C_7$ alkenyl, or $C_2$–$C_7$ alkynyl may be substituted with halo or hydroxy, and
  any one of which heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl ($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)- groups may be substituted with one or more moieties selected from the group consisting of $C_1$–$C_6$ alkyl, hydroxy, $C_1$–$C_6$ alkoxy, phenyl, naphthyl, phenyl($C_1$–$C_6$ alkylenyl)-, naphthyl ($C_1$–$C_6$ alkylenyl)-, halo, trifluoromethyl, $C_2$–$C_7$ alkenyl, $C_2$–$C_7$ alkynyl, $C_1$–$C_6$ alkoxy, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, $C_1$–$C_6$ alkylthio, amino, and nitro, and;

or a pharmaceutically acceptable salt or solvate thereof.

This invention also encompasses, in additional embodiments, the novel compounds of Formula I, and the salts and solvates thereof, as well as pharmaceutical formulations comprising a compound of Formula I, or a pharmaceutically acceptable salt or solvate thereof, in combination with one or more pharmaceutically acceptable carriers, excipients, or diluents therefor.

DETAILED DESCRIPTION AND PREFERRED EMBODIMENTS

The current invention concerns the discovery that a select group of substituted 1H-naphth[2,3-d]imidazoles, those of Formula I, are useful as neuropeptide Y receptor antagonists.

The terms and abbreviations used in the instant examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "MS" refers to mass spectrometry; "IR" refers to infrared spectroscopy; and "NMR" refers to nuclear magnetic resonance spectroscopy.

As used herein, the term "$C_1$–$C_{12}$ alkyl" refers to straight or branched, monovalent, saturated aliphatic chains of 1 to 12 carbon atoms and includes, but is not limited to, methyl, ethyl, propyl, isopropyl, butyl, isobutyl, t-butyl, pentyl, isopentyl, and hexyl. The term "$C_1$–$C_{12}$ alkyl" includes within its definition the terms "$C_1$–$C_6$ alkyl" and "$C_1$–$C_4$ alkyl".

"$C_2$–$C_7$ alkanoyloxy" represents a straight or branched alkyl chain having from one to six carbon atoms attached to a carbonyl moiety joined through an oxygen atom. Typical $C_2$–$C_7$ alkanoyloxy groups include acetoxy, propanoyloxy, isopropanoyloxy, butanoyloxy, t-butanoyloxy, pentanoyloxy, hexanoyloxy, 3-methylpentanoyloxy and the like.

"$C_3$–$C_8$ cycloalkyl" represents a saturated hydrocarbon ring structure containing from three to eight carbon atoms. Typical $C_3$–$C_8$ cycloalkyl groups include cyclopropyl, cyclopentyl, cyclohexyl, cycloheptyl, and the like.

The term "carbamoyl" as employed herein refers to a group of the structure —NH—C(O)O—.

"Halo" represents chloro, fluoro, bromo or iodo.

The term "$C_1$–$C_6$ haloalkyl" refers to a straight or branched, monovalent, saturated aliphatic chains of 1 to 6 carbon atoms substituted with one or more halo groups.

"$C_1$–$C_{10}$ alkylthio" represents a straight or branched alkyl chain having from one to ten carbon atoms attached to a sulfur atom. Typical $C_1$–$C_{10}$ alkylthio groups include methylthio, ethylthio, propylthio, isopropylthio, butylthio and the like. The term "$C_1$–$C_{10}$ alkylthio" includes within its definition the term "$C_1$–$C_6$ alkylthio" and "$C_1$–$C_3$ alkylthio".

"$C_1$–$C_{12}$ alkylenyl" refers to a straight or branched, divalent, saturated aliphatic chains of 1 to 12 carbon atoms and includes, but is not limited to, methylenyl, ethylenyl, propylenyl, isopropylenyl, butylenyl, isobutylenyl, t-butylenyl, pentylenyl, isopentylenyl, hexylenyl, octylenyl, 3-methyloctylenyl, decylenyl. The term "$C_1$–$C_6$ alkylenyl" is encompassed within the term "$C_1$–$C_{12}$ alkylenyl".

"$C_1$–$C_{10}$ alkylamino" represents a group of the formula

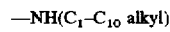

—NH($C_1$–$C_{10}$ alkyl)

wherein a chain having from one to ten carbon atoms is attached to an amino group. Typical $C_1$–$C_4$ alkylamino groups include methylamino, ethylamino, propylamino, isopropylamino, butylamino, sec-butylamino and the like.

The term "$C_2$–$C_{10}$ alkenyl" as used herein represents a straight or branched, monovalent, unsaturated aliphatic chain having from two to ten carbon atoms. Typical $C_2$–$C_{10}$ alkenyl groups include ethenyl (also known as vinyl), 1-methylethenyl, 1-methyl-1-propenyl, 1-butenyl, 1-hexenyl, 2-methyl-2-propenyl, 1-propenyl, 2-propenyl, 2-butenyl, 2-pentenyl, and the like.

The term "$C_2$–$C_{10}$ alkynyl" as used herein represents a straight or branched, monovalent, unsaturated aliphatic chain having from two to ten carbon atoms with at least one triple bond. Typical $C_2$–$C_{10}$ alkynyl groups include ethynyl, 1-methylethenyl, 1-propynyl, 1-butynyl, 1-hexynyl, 2-propynyl, 2-butynyl, 2-pentynyl, and the like.

"$C_3$–$C_8$ cycloalkenyl" represents a hydrocarbon ring structure containing from three to eight carbon atoms and having at least one double bond within that ring, which is unsubstituted or substituted with 1, 2 or 3 substituents independently selected from halo, halo($C_1$–$C_4$ alkyl), $C_1$–$C_4$ alkyl, $C_1$–$C_4$ alkoxy, carboxy, $C_1$–$C_4$ alkoxycarbonyl, carbamoyl, N—($C_1$–$C_4$ alkyl)carbamoyl, amino, $C_1$–$C_4$ alkylamino, di($C_1$–$C_4$ alkyl)amino or —(CH$_2$)$_a$—R$^y$ where a is 1, 2, 3 or 4 and R$^y$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$ alkyl)amino.

"$C_1$–$C_6$ alkylamino" represents a straight or branched alkylamino chain having from one to six carbon atoms attached to an amino group. Typical $C_1$–$C_6$ alkyl-amino groups include methylamino, ethylamino, propylamino, isopropylamino, butylamino, sec-butylamino and the like. "$C_1$–$C_6$ alkylamino" encompasses within this term "$C_1$–$C_4$ alkylamino".

"$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_3$ alkoxy".

"$C_2$–$C_7$ alkanoyl" represents a straight or branched alkyl chain having from one to six carbon atoms attached to a carbonyl moiety. Typical $C_2$–$C_7$ alkanoyl groups include ethanoyl, propanoyl, isopropanoyl, butanoyl, t-butanoyl, pentanoyl, hexanoyl, 3-methylpentanoyl and the like.

"$C_1$–$C_6$ alkoxycarbonyl" represents a straight or branched alkoxy chain having from one to six carbon atoms attached to a carbonyl moiety. Typical $C_1$–$C_6$ alkoxycarbonyl groups include methoxycarbonyl, ethoxycarbonyl, propoxycarbonyl, isopropoxycarbonyl, butoxycarbonyl, t-butoxycarbonyl and the like.

"$C_3$-$C_8$ cycloalkyl" represents a saturated hydrocarbon ring structure containing from three to eight carbon atoms. Typical $C_3$-$C_8$ cycloalkyl groups include cyclopropyl, cyclopentyl, cyclohexyl, cycloheptyl, and the like.

In those substitutions employing naphthyl, naphthyloxy, naphthoyl, or the like groups, the naphthyl moiety may be attached at the one, two, or three position.

The term "heterocycle" represents an unsubstituted or substituted stable 5- to 7-membered monocyclic or 7- to 10-membered bicyclic heterocyclic ring which is saturated and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The hetero-cycle is unsubstituted or substituted with 1, 2 or 3 substituents independently selected from halo, halo($C_1$-$C_4$)-alkyl, $C_1$-$C_4$ alkyl, $C_1$-$C_4$ alkoxy, carboxy, $C_1$-$C_4$ alkoxycarbonyl, carbamoyl, N—($C_1$-$C_4$)-alkylcarbamoyl, amino, $C_1$-$C_4$ alkylamino, di($C_1$-$C_4$)alkylamino or —($CH_2$)$_a$—$R^d$ where a is 1, 2, 3 or 4; and $R^d$ is hydroxy, $C_1$-$C_4$ alkoxy, carboxy, $C_1$-$C_4$ alkoxycarbonyl, amino, carbamoyl, $C_1$-$C_4$ alkylamino or di($C_1$-$C_4$)alkylamino.

The term "unsaturated heterocycle" represents an unsubstituted or substituted stable 5- to 7-membered monocyclic or 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, $C_1$-$C_6$ haloalkyl, $C_1$-$C_4$ alkyl, $C_1$-$C_4$ alkoxy, carboxy, $C_1$-$C_4$ alkoxycarbonyl, carbamoyl, N—($C_1$-$C_4$) alkylcarbamoyl, amino, $C_1$-$C_4$ alkylamino, di($C_1$-$C_4$) alkylamino or —($CH_2$)$_a$—$R^e$ where a is 1, 2, 3 or 4; and $R^e$ is hydroxy, $C_1$-$C_4$ alkoxy, carboxy, $C_1$-$C_4$ alkoxycarbonyl, amino, carbamoyl, $C_1$-$C_4$ alkylamino or di($C_1$-$C_4$) alkylamino.

Examples of such heterocycles and unsaturated heterocycles include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinyl-sulfoxide, thiamorpholinylsulfone, oxadiazolyl, triazolyl, tetrahydroquinolinyl, tetrahydrisoquinolinyl, 4,5-dihydrothiazolyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 4,8-dimethyl-naphthyl, 2-methyl-1,2,3,4-tetrahydroisoquinolinyl, N-methyl-quinolin-2-yl, 2-t-butoxycarbonyl-1,2,3,4-isoquinolin-7-yl and the like.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl, and urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl group, 2-nitrophenylsulfenyl, diphenylphosphine oxide and like amino-protecting groups. The species of amino-protecting group employed is usually not critical so long as the derivatized amino group is stable to the condition of subsequent reactions on other positions of the intermediate molecule and can be selectively removed at the appropriate point without disrupting the remainder of the molecule including any other amino-protecting groups. Preferred amino-protecting groups are trityl, t-butoxycarbonyl (BoC), allyloxycarbonyl and benzyloxycarbonyl. Further examples of groups referred to by the above terms are described by E. Haslam, "Protective Groups in Organic Chemistry", (J. G. W. McOmie, ed., 1973), at Chapter 2; and T. W. Greene and P. G. M. Wuts, PROTECTIVE GROUPS IN ORGANIC SYNTHESIS, (1991), at Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, 2-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, supra, at Chapter 5, and T. W. Greene, et al. supra, at Chapter 5.

The term "hydroxy-protecting groups" as used herein refers to substitents of the hydroxy group commonly employed to block or protect the hydroxy functionality while reacting other functional groups on the compound. Examples of such hydroxy-protecting groups include methoxymethyl, benzyloxymethyl, methoxyethoxymethyl, 2-(trimethylsilyl)ethoxymethyl, methylthiomethyl, 2,2-dichloro-1,1-difluoroethyl, tetrahydropyranyl, phenacyl, cyclopropylmethyl, allyl, $C_1$–$C_6$ alkyl, 2,6-dimethylbenzyl, o-nitrobenzyl, 4-picolyl, dimethylsilyl, t-butyldimethylsilyl, levulinate, pivaloate, benzoate, dimethylsulfonate, dimethylphosphinyl, isobutyrate, adamantoate and tetrahydropyranyl. Further examples of these groups may be found in T. W. Greene and P. G. M. Wuts, PROTECTIVE GROUPS IN ORGANIC SYNTHESIS, (1991) at Chapter 3.

The compounds of the present invention may have one or more asymmetric centers. As a consequence of these chiral centers, those compounds of the present invention occur as racemates, mixtures of enantiomers and as individual enantiomers, as well as diastereomers and mixtures of diastereomers. All asymmetric forms, individual isomers and combinations thereof, are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in NOMENCLATURE OF ORGANIC COMPOUNDS: PRINCIPLES AND PRACTICE, (J. H. Fletcher, et al., eds., 1974) at pages 103–120.

In addition to the (R)-(S) system, the older D-L system may also be used in this document to denote absolute configuration, especially with reference to amino acids. In this system a Fischer projection formula is oriented so that the number 1 carbon of the main chain is at the top. The prefix "D" is used to represent the absolute configuration of the isomer in which the functional (determining) group is on the right side of the carbon atom at the chiral center and "L", that of the isomer in which it is on the left.

In order to preferentially prepare one optical isomer over its enantiomer, the skilled practitioner can proceed by one of two routes. The practitioner may first prepare the mixture of enantiomers and then separate the two enantiomers. A commonly employed method for the resolution of the racemic mixture (or mixture of enantiomers) into the individual enantiomers is to first convert the enantiomers to diastereomers by way of forming a salt with an optically active salt or base. These diastereomers can then be separated using differential solubility, fractional crystallization, chromatography, or like methods. Further details regarding resolution of enantiomeric mixtures can be found in J. Jacques, et al, ENANTIOMERS, RACEMATES, AND RESOLUTIONS, (1991).

In addition to the schemes described above, the practitioner of this invention may also choose an enantiospecific protocol for the preparation of the compounds of Formula I. Such a protocol employs a synthetic reaction design which maintains the chiral center present in the starting material in a desired orientation. These reaction schemes usually produce compounds in which greater than 95 percent of the title product is the desired enantiomer.

As noted supra, this invention includes methods employing the pharmaceutically acceptable salts of the compounds defined by Formula I as well as salts of the compounds of Formula II. A compound of this invention can possess a sufficiently acidic, a sufficiently basic, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycolate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole.

This invention further encompasses methods employing the pharmaceutically acceptable solvates of the compounds of Formula I. Many of the compounds of Formula I can combine with solvents such as water, methanol, ethanol and acetonitrile to form pharmaceutically acceptable solvates such as the corresponding hydrate, methanolate, ethanolate and acetonitrilate.

This invention also encompasses the pharmaceutically acceptable prodrugs of the compounds of Formula I. A prodrug is a drug which has been chemically modified and may be biologically inactive at its site of action, but which may be degraded or modified by one or more enzymatic or other in vivo processes to the parent bioactive form. This prodrug should have a different pharmacokinetic profile than the parent, enabling easier absorption across the mucosal epithelium, better salt formation or solubility, or improved systemic stability (an increase in plasma half-life, for example).

Typically, such chemical modifications include:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, DESIGN OF PRODRUGS, (1985).

The compounds of the present invention are derivatives of 1H-naphth[2,3-d]imidazole which are named and numbered according to the RING INDEX, The American Chemical Society, as follows.

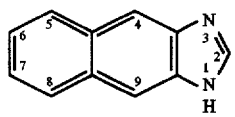

The preferred methods of this invention employ those compounds of Formula I wherein:

a) $R^1$ is phenyl, naphthyl, phenyl($C_1$–$C_6$ alkylenyl)-, naphthyl($C_1$–$C_6$ alkylenyl)-, phenyl($C_1$–$C_6$ alkoxy)-, naphthyl($C_1$–$C_6$ alkoxy)-, phenoxy($C_1$–$C_6$ alkylenyl)-, naphthyloxy($C_1$–$C_6$ alkylenyl)-, or substituted derivatives thereof; and b) $R^2$ is phenyl, heterocyclic, unsaturated heterocyclic, phenyl($C_1$–$C_6$ alkylenyl)-, naphthyl($C_1$–$C_6$ alkylenyl)-, phenyl($C_1$–$C_6$ alkoxy)-, heterocyclic($C_1$–$C_6$ alkylenyl) -, unsaturated heterocyclic($C_1$–$C_6$ alkylenyl)-, heterocyclic($C_1$–$C_6$ alkoxy)-, unsaturated heterocyclic ($C_1$–$C_6$ alkoxy)-, —$(CH_2)_2$—$NR^7R^8$, or substituted derivatives thereof;

The preferred compounds of this invention are those compounds which are employed in the preferred methods of this invention.

In the scientific literature derivatives of 1H-naphth[2,3-d]imidazole are already known to possess different biological activities, such as antineoplastic activity (U.S. Pat. No. 5,360,803) and as a treatment for gastric ulcers (U.S. Pat. No. 4,248,880). These compounds have traditionally been used as photographic dyes and sensitizers.

The compounds of Formula I can be prepared by processes known in the literature. See, e.g., G. W. H. Cheeseman and R. F. Cookson, THE CHEMISTRY OF HETERO-CYCLIC COMPOUNDS, (A. Weissberger, et al., eds. 1979). One such synthesis scheme is depicted below.

Synthesis of the 1H-Naphth[2,3-d]imidazole Nucleus

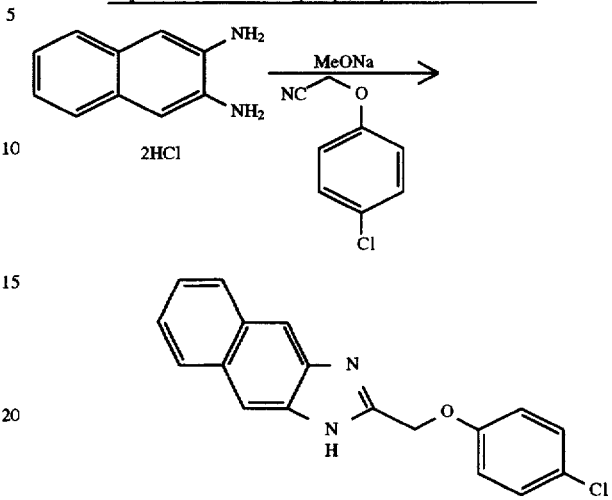

The 2,3-diaminonaphthalene described above may be prepared using standard techniques, such as those described in U.S. Pat. No. 4,248,880, the entire contents of which are herein incorporated by reference. In one such procedure 2,3-dihydroxynaphthalene is suspended in 25% ammonia and shaken under a nitrogen atmosphere to produce the 2,3-diaminonaphthalene. The hydrochloride salt of this is then made by bubbling hydrogen chloride gas through a suspension of the 2,3-diaminonaphthalene in methanol using standard techniques.

(Scheme I)
Synthesis of the N-1 Substituted 1H-naphth[2,3-d]imidazoles

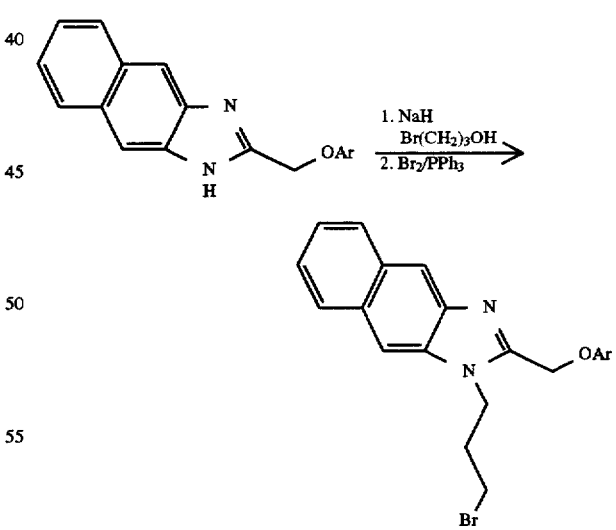

-continued
(Scheme I)
Synthesis of the N-1 Substituted 1H-naphth[2,3-d]imidazoles

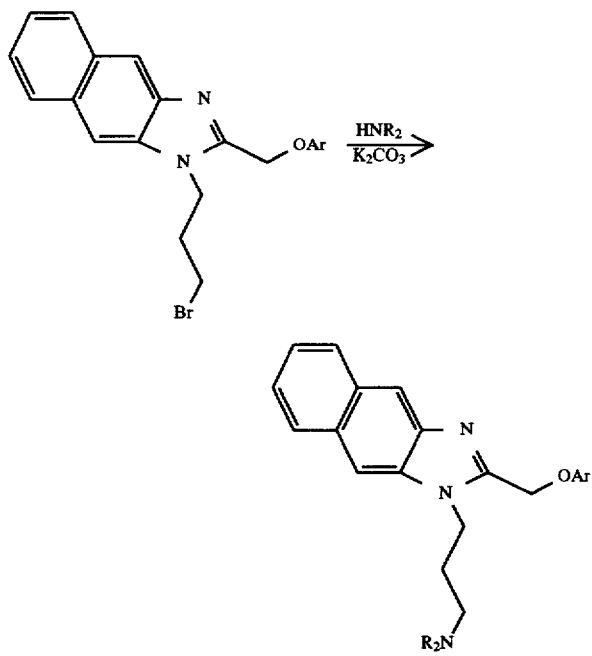

(Scheme II)
Synthesis of the N-1 Substituted 1H-naphth[2,3-d]imidazoles

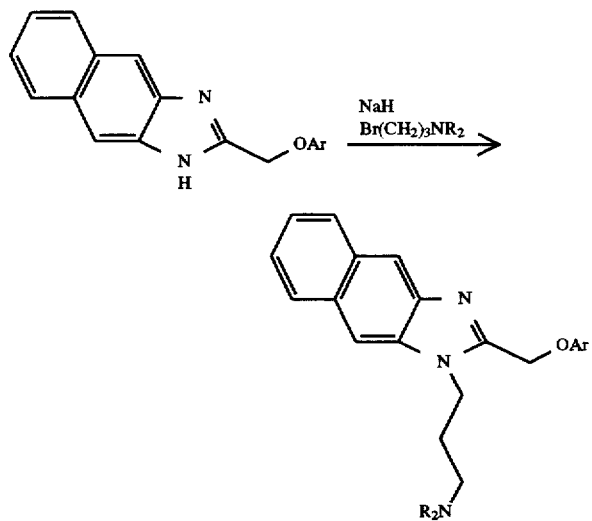

Another means of preparing the compounds of Formula I is by cyclization of an appropriately substituted 2,3-diaminonaphthalene such as the one depicted in Formula II

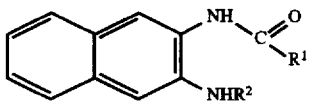

II in a solvent or solvent mixture. It is generally preferred that the solvent or solvent mixture be heated, preferably to the boiling point of the solvent. Suitable solvents include ethanol, isopropanol, glacial acetic acid, benzene, toluene, chlorobenzene, glycol, ethylene glycol, dimethyl ether, diethyl ether, dimethylformamide, chloroform, ethyl acetate, and the like. It is generally preferred to add a condensation agent such as phosphorous oxychloride, thionyl chloride, p-toluenesulfonic acid, hydrochloric acid, sulfuric acid, phosphoric acid, polyphosphoric acid, phosphorous pentoxide, methanesulfonyl hydroxide, methanesulfonyl chloride, and the like. The cyclization reaction may also optionally be performed in the presence of a base such as sodium hydroxide, sodium mesylate, or potassium tert-butylate.

In those compounds in which $R^2$ is phenyl a derivative of N-phenyl-2,3-diaminonaphthalene was used as the starting material for the cyclization reaction.

Those compounds of Formula I wherein $R^2$ is alkyl or substituted alkyl may alternatively be prepared by the direct alkylation of a 1H-naphth[2,3-d]imidazole wherein the nitrogen at the 1-position is substituted with a hydrogen. This type of alkylation is usually performed by the reaction of the 1H-naphth[2,3-d]imidazole with an alkyl halide in the presence of a strong base, such as sodium hydride. This reaction is usually performed in a polar aprotic solvent, such as N,N-dimethylformamide, dimethyl sulfoxide, dimethylacetamide, hexamethylphosphoric triamide, and the like.

The following Examples further illustrate the compounds of the present invention and the methods for their synthesis. The Examples are not intended to be limiting to the scope of the invention in any respect, and should not be so construed. All experiments were run under a positive pressure of dry nitrogen or argon. All solvents and reagents were purchased from commercial sources and used as received, unless otherwise indicated. Dry tetrahydrofuran (THF) was obtained by distillation from sodium or sodium benzophenone ketyl prior to use.

Proton nuclear magnetic resonance ($^1$H NMR) spectra were obtained on a GE QE-300 spectrometer at 300.15 MHz, a Bruker AM-500 spectrometer at 500 MHz, or a Bruker AC-200P spectrometer at 200 MHz. (Unless designated otherwise, the term "NMR" as employed herein refers to proton nuclear magnetic resonance.) Free atom bombardment mass spectroscopy (FAB) was performed on a VG ZAB-2SE instrument.

Field desorption mass spectroscopy (FDMS) was performed using either a VG 70SE or a Varian MAT 731 instrument.

Optical rotations were measured with a Perkin-Elmer 241 polarimeter. Chromatographic separation on a Waters Prep 500 LC was generally carried out using a linear gradient of the solvents indicated in the text unless otherwise specified.

The reactions were generally monitored for completion using thin layer chromatography (TLC). Thin layer chromatography was performed using E. Merck Kieselgel 60 $F_{254}$ plates, 5 cm×10 cm, 0.25 mm thickness. Spots were detected using a combination of UV and chemical detection (plates dipped in a ceric ammonium molybdate solution [75 g of ammonium molybdate and 4 g of cerium (IV) sulfate in 500 ml of 10% aqueous sulfuric acid] and then heated on a hot plate). Preparative centrifugal thin layer chromatography was performed on a Harrison Model 7924A Chromatotron using Analtech silica gel GF rotors.

Cation exchange chromatography was performed with Dowex® 50X8-100 ion exchange resin. Anion exchange chromatography was performed with Bio-Rad AG® 1-X8 anion-exchange resin (acetate form converted to hydroxide form). Flash chromatography was performed as described by Still, et al., *Journal of Organic Chemistry*, 43:2923 (1978).

Optical rotations are reported at the sodium-D-line (354 nm). Elemental analyses for carbon, hydrogen, and nitrogen were determined on a Control Equipment Corporation 440 Elemental Analyzer, or were performed by the Universidad Complutense Analytical Centre (Facultad de Farmacia, Madrid, Spain). Melting points were determined in open glass capillaries on a Thomas Hoover capillary melting point apparatus or a Büchi melting point apparatus, and are uncorrected.

PREPARATION 1

Preparation of (3'R) ethyl 2-(piperidin-3-yl)acetate

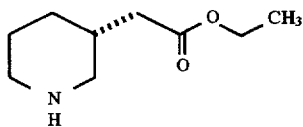

Ethyl-3-pyridylacetate (100 g, 0.606 mol) was dissolved in ethanol (1.8 liters), treated with 5% rhodium on alumina (100 g) and hydrogenated at 60° C. and 60 psi hydrogen gas overnight. The catalyst was removed by filtration and the solvent evaporated to give a brown liquid (101.4 g, 98%). The brown liquid was dissolved in ethyl acetate (600 ml) and treated with L-(+)-mandelic acid in warm ethyl acetate (600 ml). After cooling in the refrigerator for four hours, the solid was collected and the crystallization fluid reserved for processing to the other enantiomer, infra. The solid was again recrystallized from ethyl acetate (1.55–1.6 liters, overnight at ambient temperature) to give the desired title product as white needles. Yield: 81.6 grams, 41%.
O.R. (EtOH) @589 nm =+44.9°, @365 nm=+173.73°. mp 118°–119° C.

PREPARATION 2

Preparation of (3'S) ethyl 2-(piperidin-3-yl)acetate

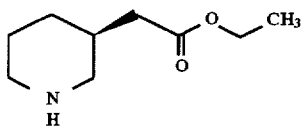

The crystallization fluid from Preparation 1, supra, was evaporated to give a dark oil (100.3 g). This was dissolved in a cold solution of potassium carbonate (52 g, 0.377 mol) in water (250 ml) and extracted with ethyl acetate (5×150 ml). The extracts were combined and dried over magnesium sulfate. The solvents were removed in vacuo to give a dark liquid (40.25 g). The dark liquid was treated with a warm solution of D-(−)-mandelic acid (36 g) in ethyl acetate (650 ml) and stirred at ambient temperatures overnight. The crystals were recrystallized twice more from ethyl acetate (1.2 liters and 1.1 liters, respectively) to give the desired title product as white needles. Yield: 48.7 g, 24.9%.
O.R. (EtOH) @589 nm =−43.14°, @365 nm =−164.31°. mp 115.5°–117° C.

Chiral Analytical Method

Cold aqueous potassium carbonate (0.15 g in 10 ml of water) was treated with 0.3 g of the mandelic acid salt and the mixture was extracted with ethyl acetate (3×5 ml). The combined extracts were dried over magnesium sulfate and the solvents were removed in vacuo. The residue was dissolved in diethyl ether (10 ml) and treated with S-(−)-α-methylbenzylisocyanate (0.12 ml). After 2.5 hours, the reaction was treated wtih 1N hydrochloric acid (2 ml). The ether was separated and then washed sequentially with brine, a saturated aqueous sodium bicarbonate solution, and brine. The organic fraction was dried over magnesium sulfate and the solvents were removed by evaporation. The residue was analyzed on a CHIRACEL OJ™ high performance liquid chromatography column (4.6×250 mm), eluting with 5% ethanol in hexanes at a flow rate of 2.5 ml/minute. The slower component comes from the 1-(+)-mandelic acid salt and the faster from the d-(−)-mandelic acid salt. HPLC analysis of the final crystallization products of both enantiomers show less than three percent of the opposite enantiomer.

PREPARATION 3

Preparation of (3'R) ethyl 2-[N-(t-butoxycarbonyl) piperidin-3-yl]acetate

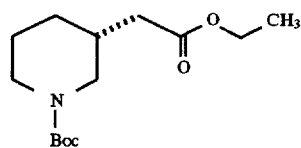

(3'R)-Ethyl 2-(piperidin-3-yl)acetate (10.9 g, 34 mmol) as prepared in Preparation 1 was dissolved in 50 ml of a 12% sodium carbonate in water solution and the resulting solution was extracted with chloroform. The extracts were dried and the solvents removed by evaporation. The residue was suspended in diethyl ether, filtered, and evaporated to give the free base (5.36 g). The liquid was dissolved in ether (50 ml) and treated dropwise with di-t-butyldicarbonate (7.9 g) in ether (10 ml). After stirring overnight, the solution was cooled in an ice water bath and treated dropwise with saturated aqueous citric acid (25 ml). The aqueous fraction was extracted with diethyl ether. The organic fractions were combined, washed with water, a saturated sodium bicarbonate solution, and then brine, and then dried over magnesium sulfate. The solvents were removed in vacuo to give the desired title product was a clear liquid. NMR was consistent with proposed title structure.

PREPARATION 4

Preparation of (3'S) ethyl 2-[N-(t-butoxycarbonyl) piperidin-3-yl]acetate

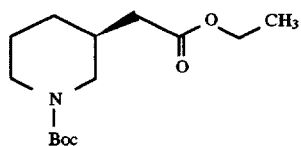

(3'S)-Ethyl 2-(piperidin-3-yl)acetate (48.6 g, 150 mmol), as prepared in Preparation 2, was treated with a solution of potassium carbonate (30 g, 0.217 mol) in water (220 ml) and the resulting solution was extracted with chloroform (3×100 ml). The extracts were dried over sodium sulfate and the solvents were removed in vacuo. The residue was mixed with diethyl ether (200 ml) and filtered to remove some suspended solids. Evaporation of the ether gave a brownish liquid (25 g, Theory=25.7 g). The residue was dissolved in diethyl ether (200 ml), cooled in an ice water bath, and a solution of di-t-butyldicarbonate (31.8 g, 0.146 mol) in ether (25 ml) was added dropwise with stirring. Cooling was removed and reaction was stirred overnight. The solution was again cooled in ice water and a solution of saturated aqueous citric acid (100 ml) was added dropwise. The organics were washed with brine, a saturated aqueous sodium bicarbonate solution, then brine, and then dried over sodium sulfate. The solvents were removed in vacuo to give the desired title product as a clear liquid (38.6 g, >99%). NMR was consistent with desired title structure.

PREPARATION 5

Preparation of ethyl 3-[pyrid-3-yl]prop-2-enoate

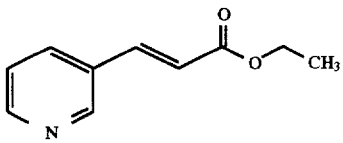

A solution of ethylphosphinoacetate (98.6 g, 0.44 mol) in dry tetrahydrofuran (1200 ml) was treated with 60% sodium hydride (17.5 g, 0.44 mol). The mixture was stirred at room temperature for two hours and was then cooled down to 0° C. To this mixture 3-pyridine carboxaldehyde (38.9 g, 0.36 mol) was added and the resulting reaction mixture was stirred for 1-2 hours while warming to room temperature. The progress of the reaction was monitored by thin layer chromatography.

Water (1000 ml) was added to the reaction mixture. The organic fraction was extracted with ethyl acetate (3×1000 ml). The organic fractions were combined, washed with water (2×1000 ml), brine (1×1000 ml), and the dried over sodium sulfate. The solvents were removed in vacuo to yield 62.5 grams (97%) of the desired title product.

PREPARATION 6

Preparation of (RS) ethyl 3-[piperidin-3-yl] propionate

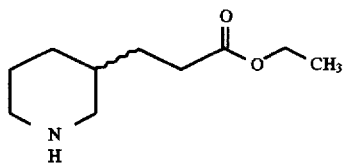

A solution of ethyl 3-[pyrid-3-yl]prop-2-enoate (60 g, 0.34 mol) in ethanol (600 ml) was treated with 5% rhodium on alumina powder (17.2 g). The mixture was placed under a hydrogen atmosphere (55 psi) for five hours at 60° C. The reaction was stopped by removing the hydrogen and the reaciton mixture was filtered through a layer of CELITE™. The residue was washed with hot ethanol. The filtrate was concentrated and purified by flash chromatography to provide 39.6 grams (63%) of the desired title product.

IR, NMR, and IR were consistent with the proposed title structure.

PREPARATION 7

Preparation of (3'S) ethyl 3-[piperidin-3-yl] propionate mandelic acid salt

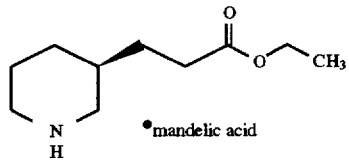

A solution of (RS) ethyl 3-[piperidin-3-yl]propionate (52.0 g, 281 mmol) in hot ethyl acetate (300 ml) was added to the hot solution of R-(-) mandelic acid (42.7 g, 281 mmol). The resulting mixture was then filtered and the clear solution was left at room temperature overnight. The newly formed white crystals of the salt were filtered from the solution. These crystals were recrystallized twice by dissolution in hot ethyl acetate (300 ml) and letting it cool down to room temperature each time. The final pure crystals were dried to yield 33.1 grams (70%).

NMR and IR were consistent with the desired title product. The conformation about the chiral center was confirmed by X-ray crystallography.

PREPARATION 8

Preparation of (3'R) ethyl 3-[piperidin-3-yl] propionate mandelic acid salt

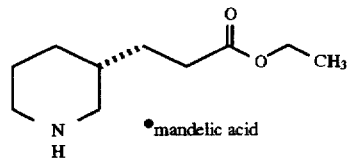

The title compound was prepared essentially as described in Preparation 7, supra, except that S-(+) mandelic acid was employed instead of the R-(-) mandelic acid employed therein.

NMR and IR were consistent with the desired title product.

PREPARATION 9

Preparation of (3'S) ethyl 3-[piperidin-3-yl] propionate

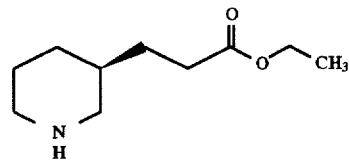

A suspension of (3'S) ethyl 3-[piperidin-3-yl]propionate mandelic acid salt (33.1 g, 98 mmol) in ethyl acetate (500 ml) was treated with a 30% aqueous solution of potassium carbonate until all the organic layer was clear. The mixture was poured into a separatory funnel and the organic fraction was extracted with ethyl acetate (3×300 ml). The combined organic fraction was washed with water (2×300 ml), then brine (1×300 ml), and then dried over sodium sulfate. The solvents were removed in vacuo to yield an oily product in nearly 100% yield.

NMR and IR were consistent with the desired title product.

PREPARATION 10

Preparation of (3'R) ethyl 3-[piperidin-3-yl]propionate

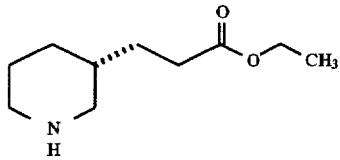

The title compound was prepared essentially as described in Preparation 9, supra, except that (3R) ethyl 3-[piperidin-3-yl]propionate mandelic acid salt was employed instead of the (3'S) ethyl 3-[piperidin-3-yl]propionate mandelic acid salt therein.

NMR and IR were consistent with the desired title product.

PREPARATION 11

Preparation of (3'S) ethyl 3-[1-(t-butoxycarbonyl)piperidin-3-yl]propionate

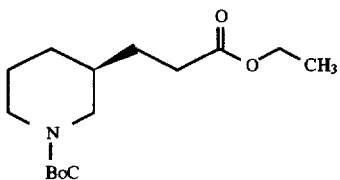

A solution of (3'S) ethyl 3-[piperidin-3-yl]propionate (12.5 g, 67.5 mmol) in tetrahydrofuran:water (2:1, 335:168 ml) was treated with potassium carbonate (14 g, 101 mmol) and di-tert-butyl dicarbonate (17.7 g, 81 mmol). The reaction mixture was stirred at room temperature for five hours. The mixture was then poured into water (200 ml). The organic fraction was extracted with ethyl acetate (3×200 ml). The organic fractions were combined, washed with water (2×200 ml) and then brine (1×200 ml), and then dried over sodium sulfate. The solvents were removed in vacuo and the title product was further purified by flash chromatography. Yield: 19.1 grams (99.2%).

NMR and IR were consistent with the desired title product.

PREPARATION 12

Preparation of (3'R) ethyl 3-[1-(t-butoxycarbonyl)piperidin-3-yl]propionate

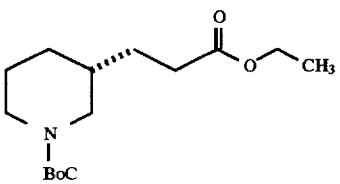

The title product was prepared essentially as described in Preparation 11, supra, except that an equimolar amount of (3'R) ethyl 3-[piperidin-3-yl]propionate was employed instead of the (3'S) ethyl 3-[piperidin-3-yl]propionate employed therein.

PREPARATION 13

Preparation of (3'S) 3-[1-(t-butoxycarbonyl)piperidin-3-yl]propanol

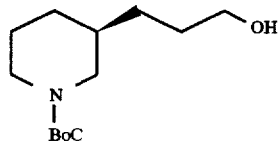

A solution of (3'S) ethyl 3-[1-(t-butoxycarbonyl)piperidin-3-yl]propionate (17.1 g, 60 mmol) in dry diethyl acetate (600 ml) was cooled to 0° C. Lithium aluminum hydride powder (2.5 g, 65 mmol) was gradually added to the mixture. The resulting mixture was stirred at 0° C. and slowly warmed to room temperature within two hours. The reaction was stopped by the slow addition of water (200 ml) and 15% aqueous sodium hydroxide (50 ml). The organic fraction was extracted with diethyl ether (3×300 ml). The combined layer was washed with water (2×200 ml) and then brine (1×200 ml) and then dried over sodium sulfate. The solvents were removed in vacuo to provide 13.2 grams (90% yield) of the title product.

NMR and IR were consistent with the desired title product.

PREPARATION 14

Preparation of (3'S) 3-[1-(t-butoxycarbonyl)piperidin-3-yl]propanol

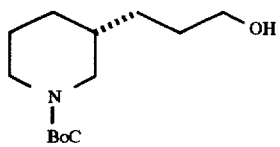

The title product was prepared essentially as described in Preparation 13, supra, except that an equimolar amount of (3'S) ethyl 3-[1-(t-butoxycarbonyl)piperidin-3-yl]propionate was employed instead of the (3'R) ethyl 3-[1-(t-butoxycarbonyl)piperidin-3-yl]propionate employed therein.

PREPARATION 15

Preparation of (3'S) 3-[1-(t-butoxycarbonyl)piperidin-3-yl]propyl bromide

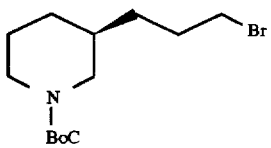

To a cold (0° C.) solution of triphenylphosphine (19.95 g, 76 mmol) in anhydrous methylene chloride (110 ml) was added bromine dropwise until the solution turned pale yellow. A few crystals of triphenylphosphine were added to the mixture to bring the color back to white. To this mixture was added a suspension of (3'S) 3-[1-(t-butoxycarbonyl)piperidin-3-yl]propanol (13.2 g, 54.4 mmol) and pyridine (8.0 g, 76 mmol) in dry methylene chloride (110 ml). The resulting mixture was stirred for five hours while warming to room temperature.

The reaction was stopped by adding water (200 ml). The organic fraction was extracted with methylene chloride (3×200 ml). The combined organic layer was washed with water (2×200 ml), then brine (1×100 ml), and then dried over sodium sulfate. The solvents were removed in vacuo to provide a light brownish crude product, which was further purified by flash chromatography to yield 11.6 grams (70%) of the desired title product.

NMR and IR were consistent with the title product.

PREPARATION 16

Preparation of (3'R) 3-[1-(t-butoxycarbonyl) piperidin-3-yl]propyl bromide

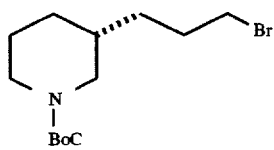

The title product was prepared essentially as described in Preparation 15, supra, except that an equimolar amount of (3'R) 3-[1-(t-butoxycarbonyl)piperidin-3-yl]propanol was employed instead of the (3'S) 3-[1-(t-butoxycarbonyl) piperidin-3-yl]propanol employed therein.

General Procedure for 1H-Naphth[2,3-d]imidazole Synthesis

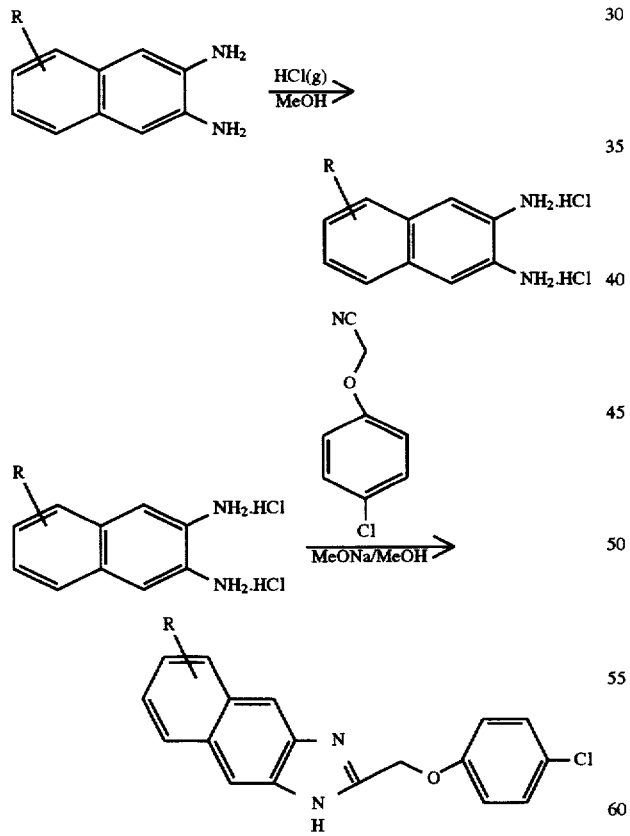

To a 0.4M solution of the optionally substituted 2,3-diaminonaphthalene in methanol, anhydrous hydrogen chloride gas was bubbled until saturation. The solution was permitted to cool to room temperature. The precipitate was collected, dried and then used in the next step.

A solution of 4-chlorophenoxynitrile (1.05 eq) in dry methanol (0.3M) was treated with sodium methoxide (1.05 eq). The mixture was stirred at room temperature. The mixture was treated with the dihydrochloride salt of the diamine (1.0 eq) and stirred at room temperature for about one hour. In most of the cases the precipitate was observed upon addition. The crude cyrstals were washed with diethyl ether and dried in vacuo.

When 2,3-diamino-7-methylnaphthalene was treated with 4-chlorophenoxynitrile there was no precipitate observed immediately. The reaction mixture was condensed under vacuum. The crude brownish solid was dissolved in ethyl acetate. The resulting solution was washed with water, then brine, and then dried over sodium sulfate. The solvents were then removed in vacuo to produce brown crystals with a good yield.

PREPARATION 17

Preparation of 2-benzylnaphth[2,3-d]imidazole

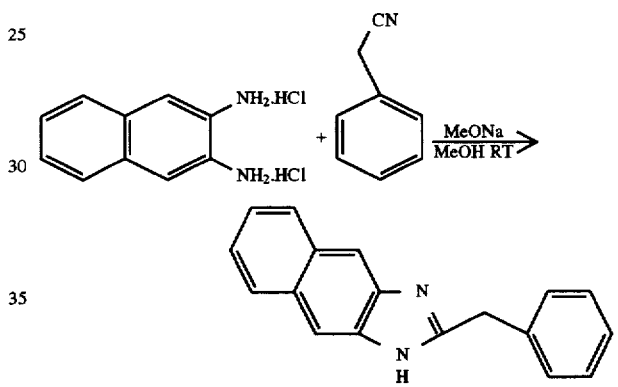

A 1M solution of benzyl cyanide in anhydrous methanol is treated with hydrogen chloride gas at 0° C. for about thirty minutes. The mixture is stirred for two hours at 0° C. and then a 1M solution of 2,3-diaminonaphthalene is added and the resulting solution is stirred at 0° C. The progress of the reaction is monitored by thin layer chromatography. The reaction mixture is then poured into water. The unreacted nitrile is extracted with ethyl acetate. The aqueous layer is neutralized with 1N sodium hydroxide. The organic fraction is extracted with ethyl acetate and condensed. The desired title product is recrystallized from methanol/water.

PREPARATION 18

Preparation of 2-(4-chlorophenyl)naphth[2,3-d] imidazole

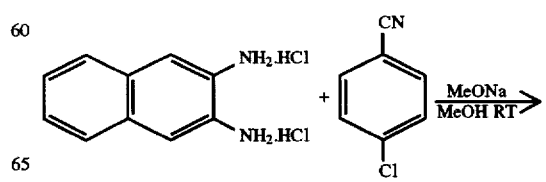

21

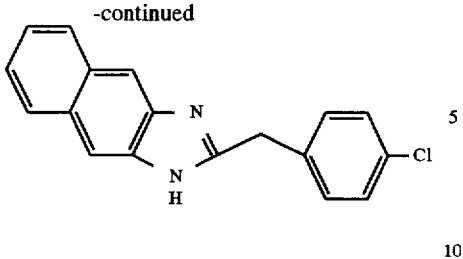

-continued

The title compound is prepared essentially as described in Preparation 1 except that an equimolar amount of 4-chlorobenzonitrile is employed instead of the benzyl cyanide employed therein.

PREPARATION 19

Preparation of 2-(4-chlorobenzyl)naphth[2,3-d]imidazole

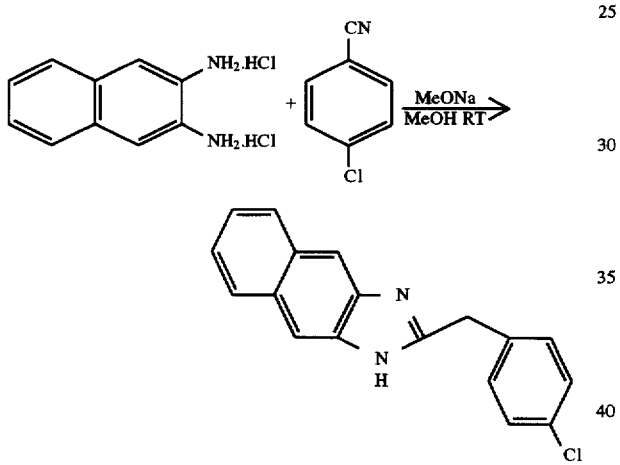

The title compound is prepared essentially as described in Preparation 1 except that an equimolar amount of 4-chlorobenzyl cyanide is employed instead of the benzyl cyanide employed therein.

PREPARATION 20

Preparation of 2-(4-chlorophenoxymethyl)naphth[2,3-d]imidazole

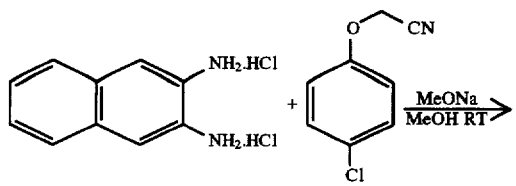

22

-continued

The title compound is prepared essentially as described in Preparation 1 except that an equimolar amount of 4-chlorophenoxymethyl cyanide is employed instead of the benzyl cyanide employed therein.

IR and NMR were consistent with the desired title product. FDMS 308 (M+).

PREPARATION 21

Preparation of 2-(benzyloxymethyl)-5-hydroxynaphth[2,3-d]imidazole and 2-(benzyloxymethyl)-8-hydroxynaphth[2,3-d]imidazole

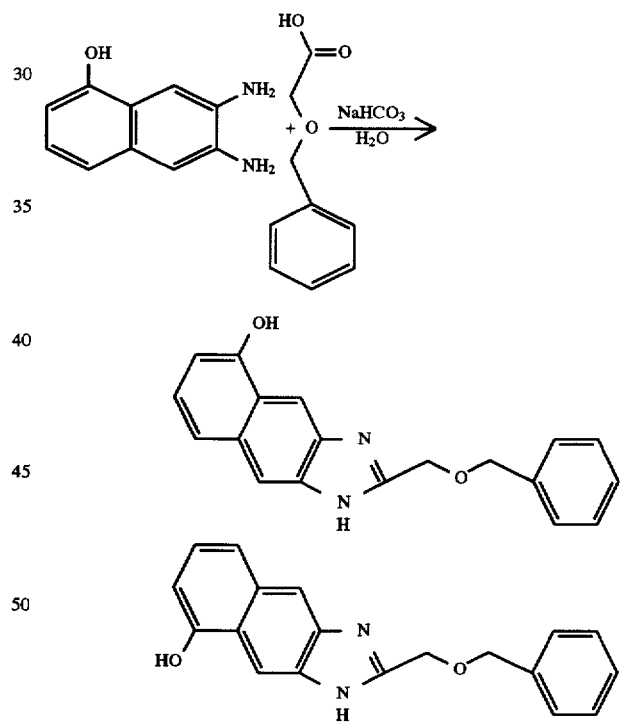

A mixture of the 6,7-diaminonaphth-1-ol (40.3 mmol, 1 eq) and benzyloxyacetic acid (5.6 g, 48.3 mmol, 1.2 eq) in 40 ml of a 10% aqueous solution of sodium bicarbonate is stirred and refluxed at 140° C. for one hour. The mixture is allowed to cool down to room temperature.

Ethyl acetate is poured into the mixture. The organic fraction is extracted with ethyl acetate, washed with water, and then dried over sodium sulfate. The solvents are removed in vacuo. The crude product is further purified by flash chromatography to yield 6.87 grams (67% yield) of the desired title product.

GENERAL PROCEDURE FOR PREPARING COMPOUNDS OF THE FORMULA

Example 1
Preparation of 2-(4-chlorophenoxymethyl)-1-(3-hydroxypropyl)-1H-naphth[2,3-d]imidazole

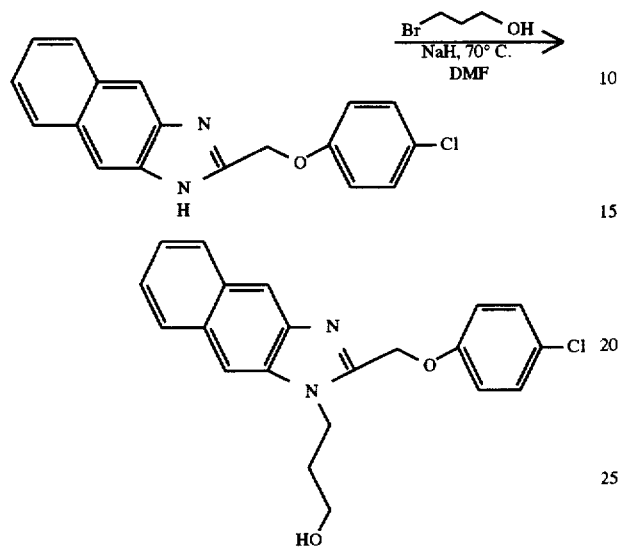

A solution of 2-(4-chlorophenoxymethyl)-1H-naphth[2,3-d]imidazole (3.9 mmol, 1.0 eq) in anhydrous N,N-dimethylformamide (10 ml) is treated with 60% disperson of sodium hydride (0.163 g, 4.1 mmol, 1.05 eq). The reaction mixture is stirred at room temperature for about thirty minutes. Bromopropanol (0.6 g, 4.3 mmol, 1.1 eq) is added to the mixture and the resulting mixture is stirred at 70° C. for five hours. The progress of the reaction is monitored by thin layer chromatography.

The reaction mixture is poured into water (20 ml). The organic fraction is extracted wtih diethyl ether (3×50 ml). The organic fractions are combined, washed with water (2×20 ml), and then brine (1×20 ml), and then dried over sodium sulfate. The solvents are removed in vacuo to yield a white solid as a crude product. No further purification is performed on this product.

The following compounds are prepared essentially as described above.

Example 2
Preparation of 2-(2,4-dichlorophenoxymethyl)-1-(3-hydroxypropyl)-1H-naphth[2,3-d]imidazole

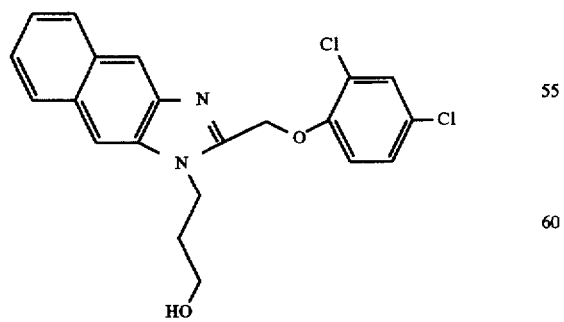

Example 3
Preparation of 2-(3,5-dichlorophenoxymethyl)-1-(3-hydroxypropyl)-1H-naphth[2,3-d]imidazole

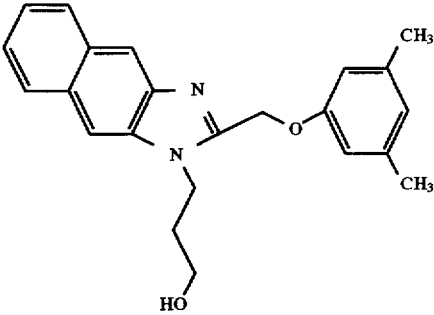

Example 4
Preparation of 2-(4-acetylbenzene)-1-(3-hydroxypropyl)-1H-naphth[2,3-d]imidazole

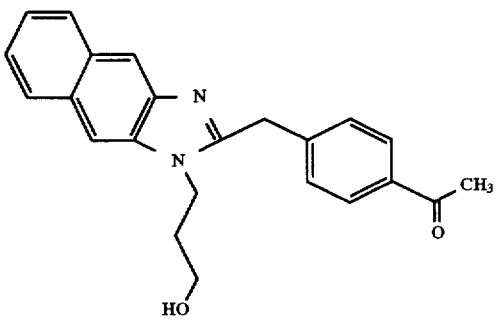

Example 5
Preparation of 2-(naphth-2-yl)-1-(3-hydroxypropyl)-1H-naphth[2,3-d]imidazole

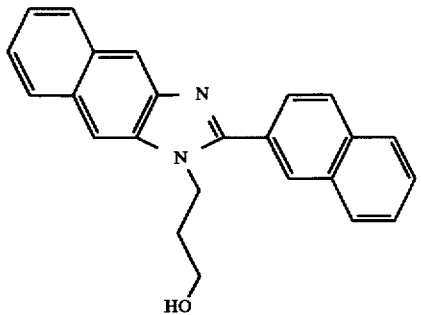

Example 6

Preparation of 2-[4-(thiazol-2-yl)benzyloxymethyl]-1-(3-hydroxypropyl)-1H-naphth[2,3-d]imidazole

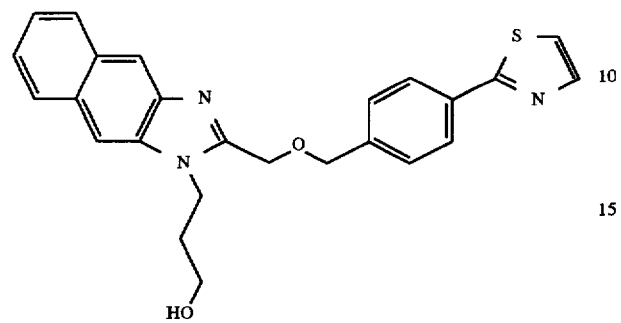

Example 7

Preparation of 2-(4-cyclohexylphenoxymethyl)-1-(3-hydroxypropyl)-1H-naphth[2,3-d]imidazole

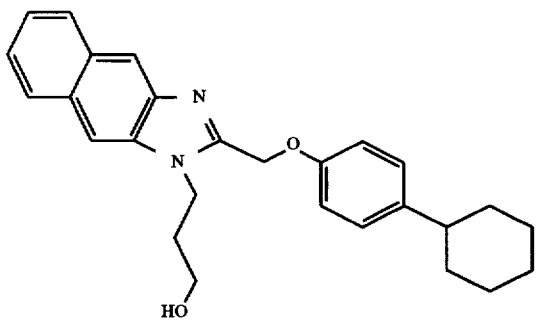

Example 8

Preparation of 2-(3-benzoylphenoxymethyl)-1-(3-hydroxypropyl)-1H-naphth[2,3-d]imidazole

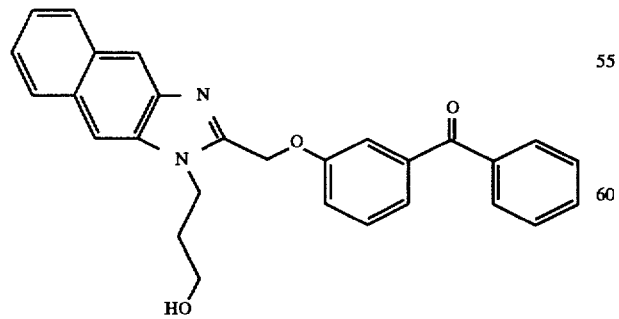

Example 9

Preparation of 2-[3-(but-2-enyl)phenoxymethyl]-1-(3-hydroxypropyl)-1H-naphth[2,3-d]imidazole

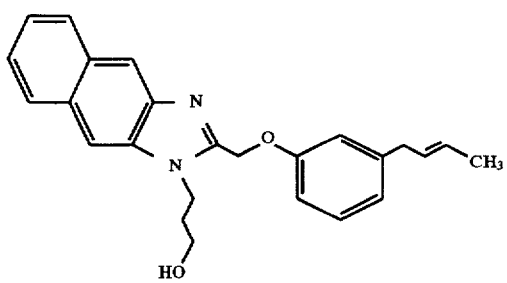

Example 10

Preparation of 2-(3,4,5-trimethoxyphenoxymethyl)-1-(3-hydroxypropyl)-1H-naphth[2,3-d]imidazole

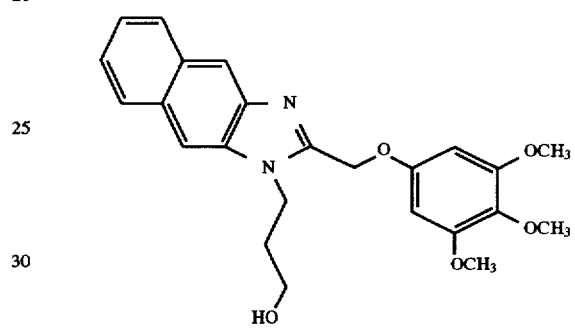

Example 11

Preparation of 2-(chlorophenoxymethyl)-1-(3-bromopropyl)-1H-naphth[2,3-d]imidazole

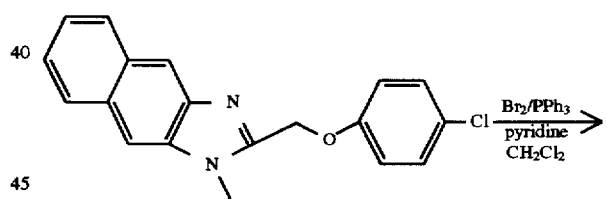

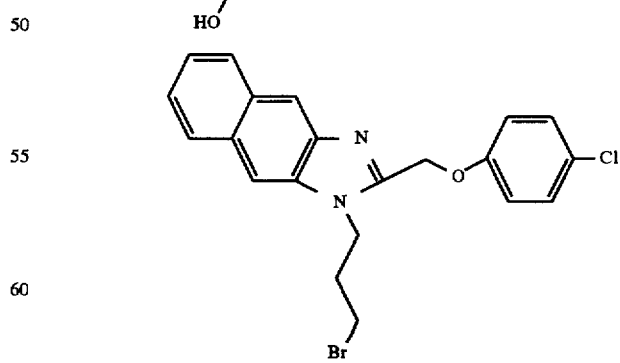

To a solution of triphenylphosphine (1.52 g, 5.8 mmol, 1.5 eq) in dry dichloromethane (10 ml) at 0° C. is added bromine solution until it is pale yellow. To the resulting mixture is added additional triphenylphosphine until the solution is white. To this mixture is then added the hydroxyalkyl-substituted naphth[2,3-d]imidazole (3.9 mmol, 1.5 eq) and pyridine (0.5 ml, 5.8 mmol, 1.5 eq) in dry dichloromethane. The resulting mixture is stirred at 0° C. and then warmed to room temperature at which temperature it is maintained for about six hours. The progress of the reaction is monitored by thin layer chromatography.

White precipitate is removed by filtration, washed with dichloromethane, and dried in vacuo to provide the crude product.

IR and NMR are consistent with the desired title product. FDMS 430 (M+).

Analysis for $C_{21}H_{18}BrClN_2O$:

Theory: C, 58.69; H, 4.22; N, 6.52.

Found: C, 50.07; H, 3.75; N, 5.57.

The following compounds are prepared essentially as described above.

Example 12

Preparation of 2-(2,4-dichlorophenoxymethyl)-1-(3-bromopropyl)-1H-naphth[2,3-d]imidazole

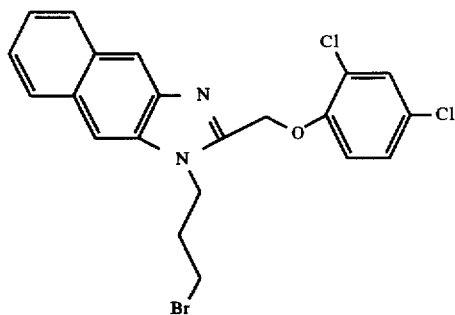

Example 13

Preparation of 2-(3,5-dichlorophenoxymethyl)-1-(3-bromopropyl)-1H-naphth[2,3-d]imidazole

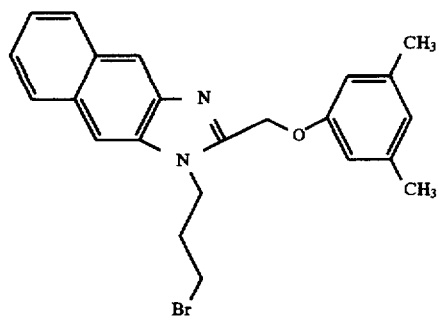

Example 14

Preparation of 2-(4-acetylbenzyl)-1-(3-bromopropyl)-1H-naphth[2,3-d]imidazole

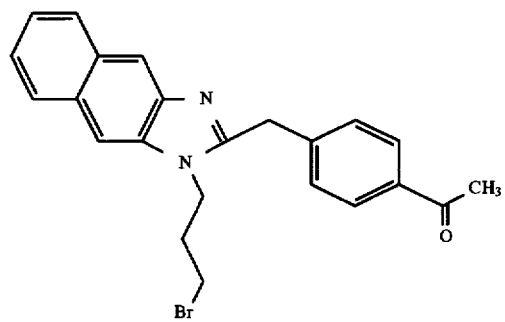

Example 15

Preparation of 2-(naphth-2-yl)-1-(3-bromopropyl)-1H-naphth[2,3-d]imidazole

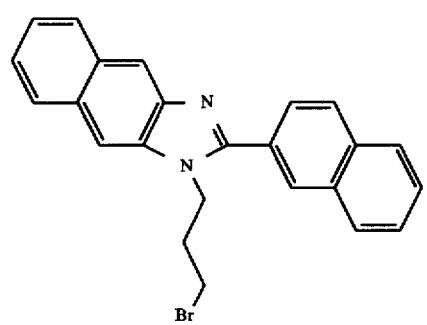

Example 16

Preparation of 2-[4-(thiazol-2-yl)benzyloxymethyl]-1-(3-bromopropyl)-1H-naphth[2,3-d]imidazole

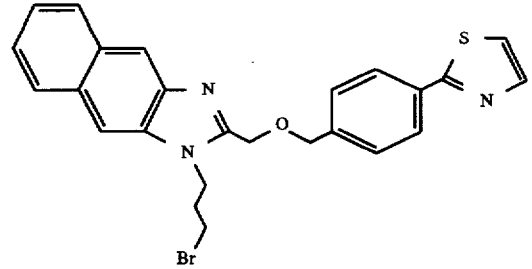

Example 17
Preparation of 2-(4-cyclohexylphenoxymethyl)-1-(3-bromopropyl)-1H-naphth[2,3-d]imidazole

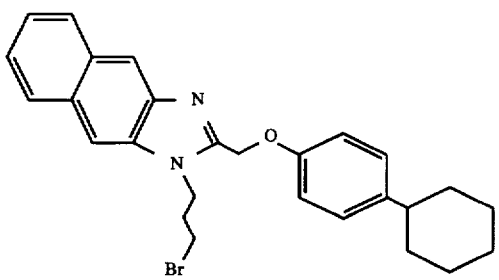

Example 18
Preparation of 2-(3-benzoylphenoxymethyl)-1-(3-bromopropyl)-1H-naphth[2,3-d]imidazole

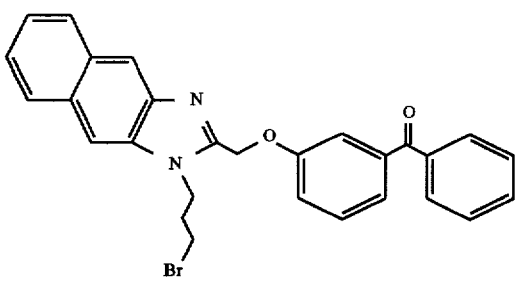

Example 19
Preparation of 2-[3-(but-2-enyl)phenoxymethyl]-1-(3-bromopropyl)-1H-naphth[2,3-d]imidazole

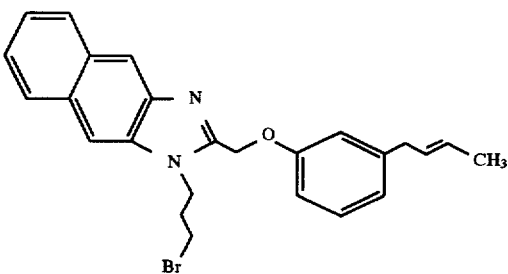

Example 20
Preparation of 2-(3,4,5-trimethoxyphenoxymethyl)-1-(3-bromopropyl)-1H-naphth[2,3-d]imidazole

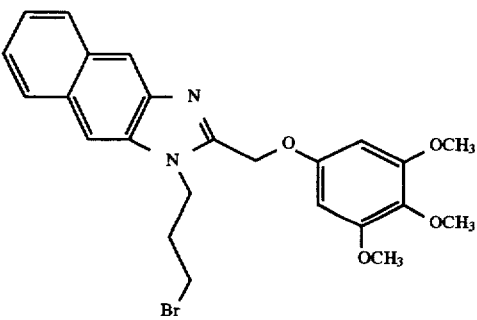

Example 21

Preparation of 2-(4-chlorophenoxy)-1-[3-(piperidin-1-yl)propyl]-1H-naphth[2,3-d]imidazole

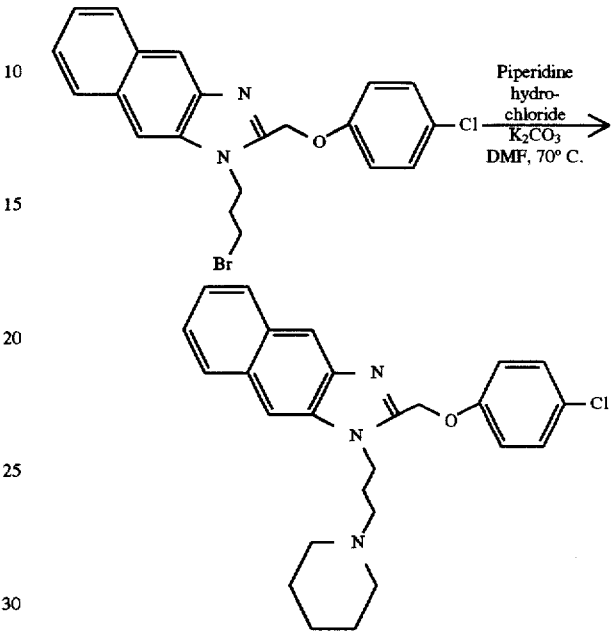

A solution of the naphthimidazole (0.26 mmol, 1.0 eq) in anhydrous N,N-dimethylformamide (2 ml) is treated with potassium carbonate (90 mg, 0.65 mmol, 2.5 eq) and piperidine hydrochloride (35 mg, 0.29 mmol, 1.1 eq). The mixture is stirred at 70° C. for about five hours. The resulting mixture is poured into water (5 ml). The organic fraction is extracted with diethyl ether (3×10 ml). The combined ether layers are washed with water (3×5 ml), then brine, and then dried over sodium sulfate. The solvents are removed in vacuo to yield an oily crude product. The desired title product is then further purified by flash chromatography.

IR and NMR are consistent with the desired title product. FDMS 434 (M+).

Analysis for $C_{26}H_{28}ClN_3O$:

Theory: C, 71.90; H, 6.58; N, 9.68.

Found: C, 71.90; H, 6.76; N, 9.40.

The following compounds are prepared essentially as described above.

Example 22

Preparation of 2-(4-chlorophenoxymethyl)-1-[3-(morpholin-1-yl)propyl]-1H-naphth[2,3-d]imidazole

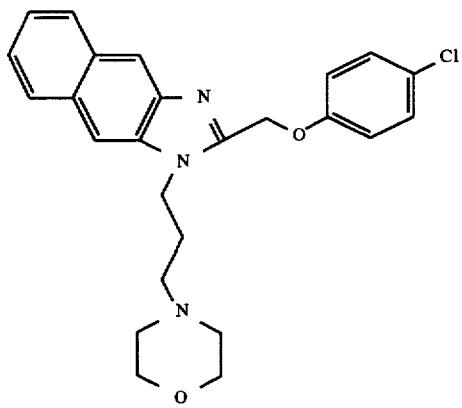

Example 23

Preparation of 2-(4-chlorophenoxymethyl)-1-[3-(piperazin-1-yl)propyl]-1H-naphth[2,3-d]imidazole

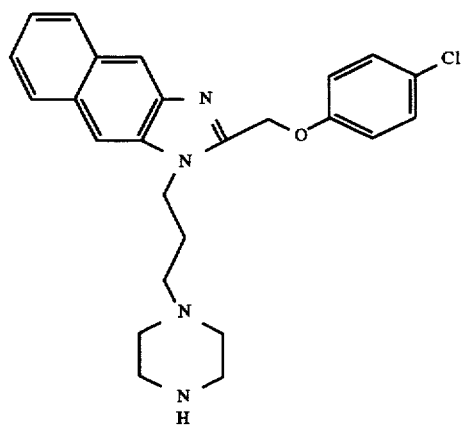

Example 25

Preparation of 2-(4-chlorophenoxymethyl)-1-[3-[4-(pyrimidin-2-yl)piperazin-1-yl]propyl]-1H-naphth[2,3-d]imidazole

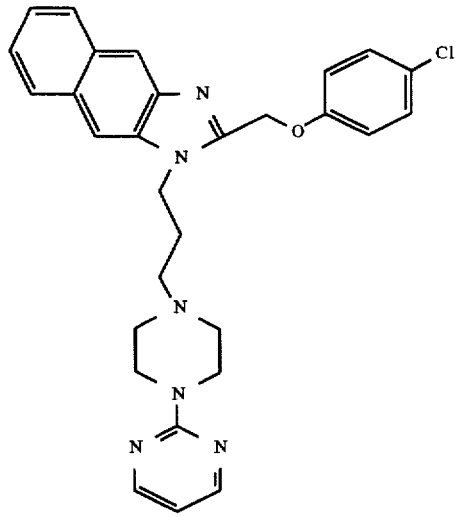

Example 25

Preparation of 2-(4-chlorophenoxymethyl)-1-[3-[4-(pyrid-2-yl)piperazin-1-yl]propyl]-1H-naphth[2,3-d]imidazole

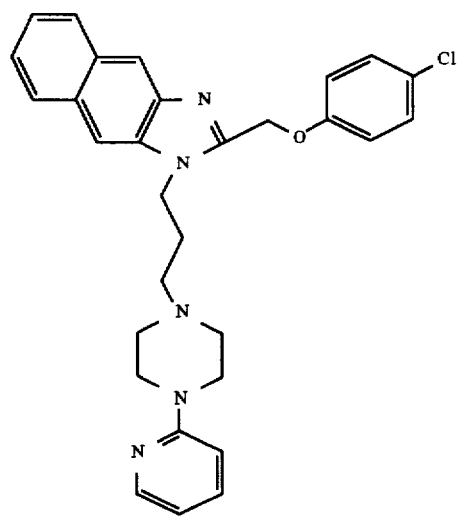

Example 26

Preparation of 2-(4-chlorophenoxymethyl)-1-[3-[4-(N,N-dimethylamino)piperidin-1-yl]propyl]-1H-naphth[2,3-d]imidazole

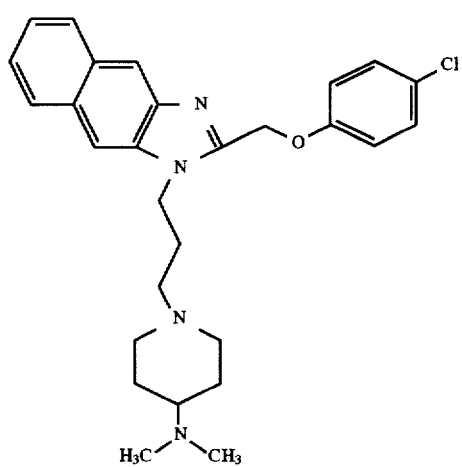

Example 27

Preparation of 2-(4-chlorophenoxymethyl)-1-[3-[4-(piperidin-1-yl)piperidin-1-yl]propyl]-1H-naphth[2,3-d]imidazole

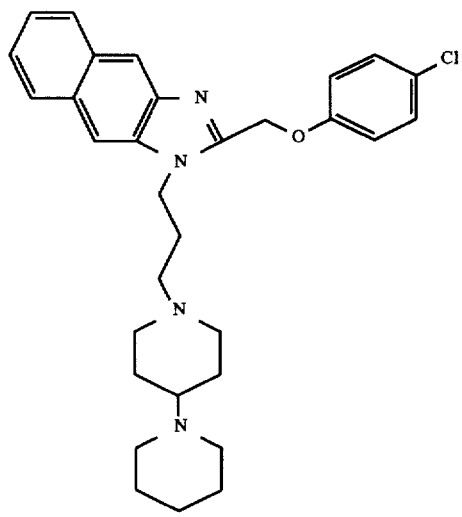

Example 28

Preparation of 2-(4-chlorophenoxymethyl)-1-[3-(4-cyclohexylpiperazin1-yl)propyl]-1H-naphth[2,3-d]imidazole

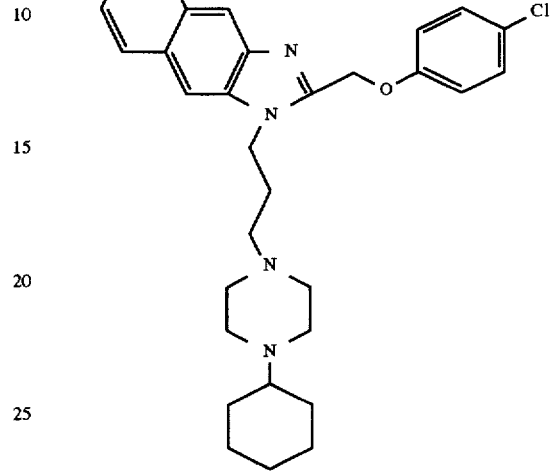

Example 29

Preparation of 2-(4-chlorophenoxymethyl)-1-[3-(4-phenylpiperazin-1-yl)propyl]-1H-naphth[2,3-d]imidazole

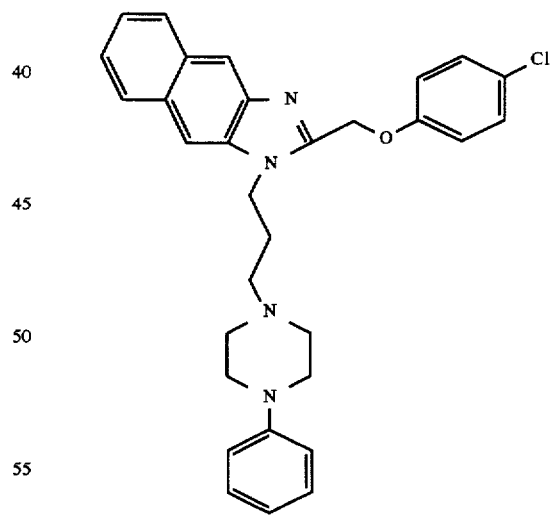

Example 30

Preparation of 2-(4-chlorophenoxymethyl)-1-[3-(fur-2-yl)propyl]-1H-naphth[2,3-d]imidazole

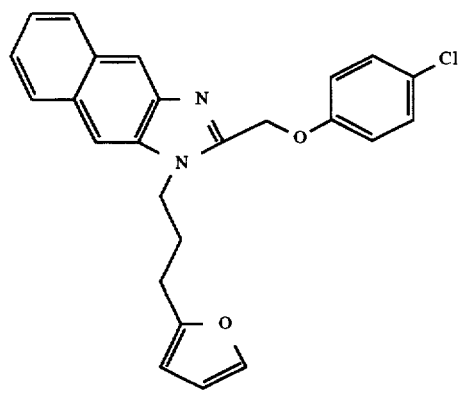

GENERAL PROCEDURE FOR PREPARING COMPOUNDS OF THE FOLLOWING FORMULAE

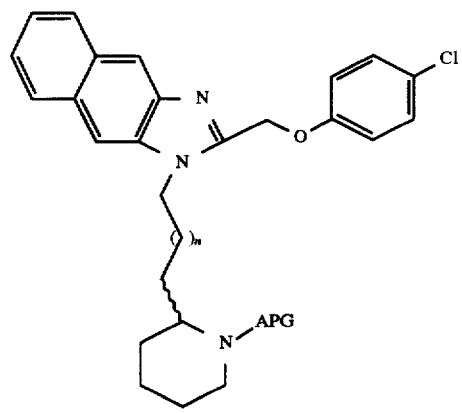

and

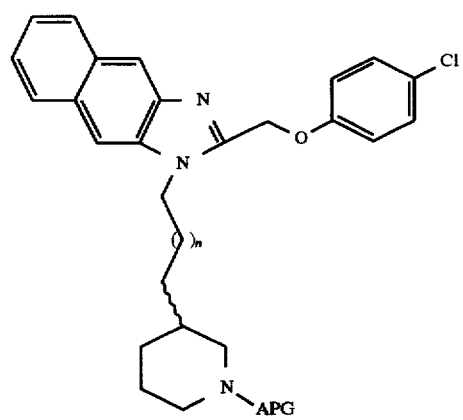

where n is 0, 1, or 2, and APG is an amino protecting group.

Example 31

Preparation of 2-(4-chlorophenoxymethyl)-1-[3-[1-(t-butoxycarbonyl)piperidin-3-yl]-1H-naphth[2,3-d]imidazole

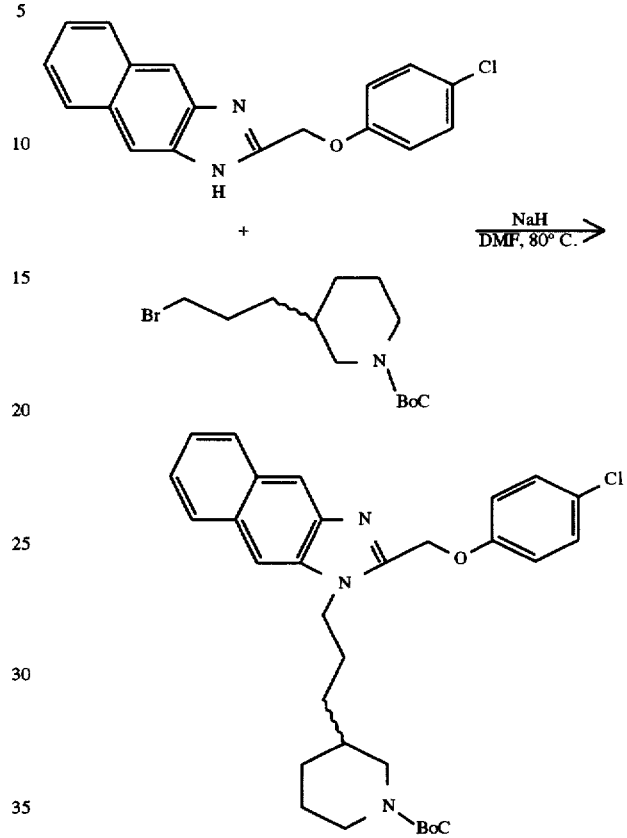

A solution of the 1-unsubstituted naphth[2,3-d]imidazole (0.77 mmol, 1.0 eq) in anhydrous N,N-dimethylformamide (3 ml) is treated with a 60% disperson of sodium hydride (33 mg, 0.80 mmol, 1.05 eq). The mixture is stirred at room temperature for thirty minutes under a stream of nitrogen. To this mixture is added [1-(t-butoxycarbonyl)piperidin-3-yl] propyl bromide (260 mg, 0.85 mmol, 1.1 eq) and the resulting mixture is stirred at 80° C. for about three hours. The progress of the reaction is monitored by thin layer chromatography.

The reaction mixture is then poured into water (10 ml). The organic fraction is extracted with diethyl ether (3×15 ml). The organic fractions are combined, washed with water (2×10 ml), brine (1×10 ml), and then dried over sodium sulfate. The solvents are removed in vacuo, leaving a light brown crude material which is further purified by flash chromatography to yield the desired title product as a white crystalline solid.

IR and NMR are consistent with the desired title product. FDMS 533, 534 (M+).

Analysis for $C_{31}H_{36}ClN_3O_3$:

Theory: C, 69.71; H, 6.79; N, 7.87.

Found: C, 69.72; H, 6.92; N, 7.80.

The following compounds are prepared essentially as described above.

Example 32

Preparation of 2-(4-chlorophenoxymethyl)-1-[3-[1-(t-butoxycarbonyl)piperidin-2-yl]propyl]-1H-naphth[2,3-d]imidazole

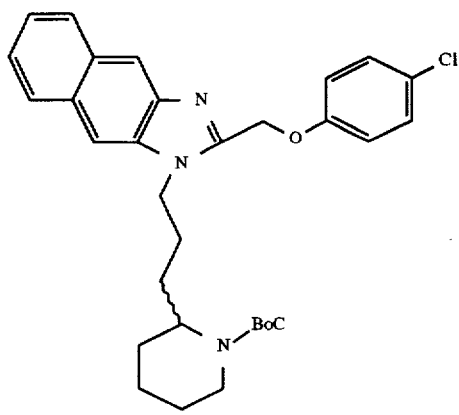

IR and NMR are consistent with the desired title product. FDMS 533, 534 (M+).

Analysis for $C_{31}H_{36}ClN_3O_3$:

Theory: C, 69.71; H, 6.79; N, 7.87.
Found: C, 70.00; H, 6.89; N, 7.63.

Example 33

Preparation of 2-(3,5-dichlorophenoxymethyl)-1-[3-[1-(t-butoxycarbonyl)piperidin-2-yl]propyl]-1H-naphth[2,3-d]imidazole

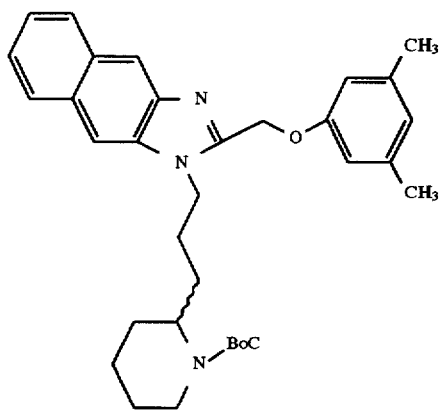

Example 34

Preparation of 2-(4-acetylbenzyl)-1-[3-[1-(t-butoxycarbonyl)piperidin-2-yl]propyl]-1H-naphth[2,3-d]imidazole

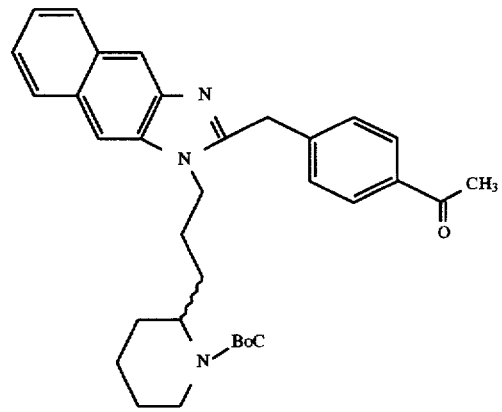

Example 35

Preparation of 2-(naphth-2-yl)-1-[3-[1-(t-butoxycarbonyl)piperidin-2-yl]propyl]-1H-naphth[2,3-d]imidazole

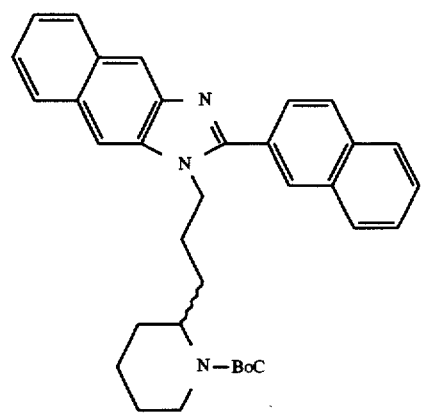

Example 36

Preparation of 2-[4-(thiazol-2-yl)benzyloxymethyl]-1-[3-[1-(t-butoxycarbonyl)piperidin-2-yl]propyl]-1H-naphth[2,3-d]imidazole

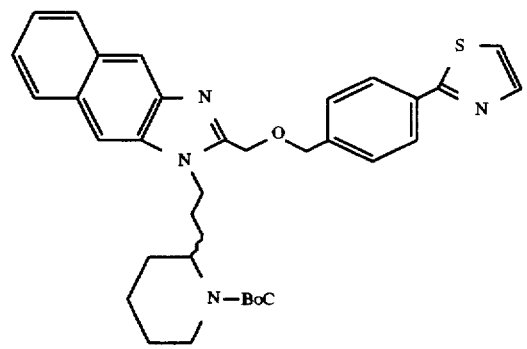

Example 37

Preparation of 2-(4-cyclohexylphenoxymethyl)-1-[3-[1-(t-butoxycarbonyl)piperidin-3-yl]propyl]-1H-naphth[2,3-d]imidazole

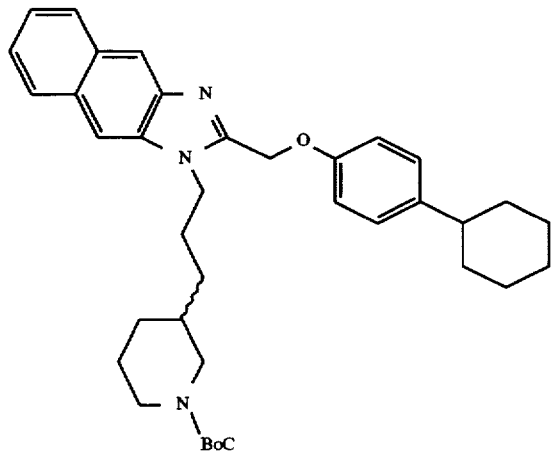

Example 38

Preparation of 2-(3-benzoylphenoxymethyl)-1-[3-[1-(t-butoxycarbonyl)piperidin-3-yl]propyl]-1H-naphth[2,3-d]imidazole

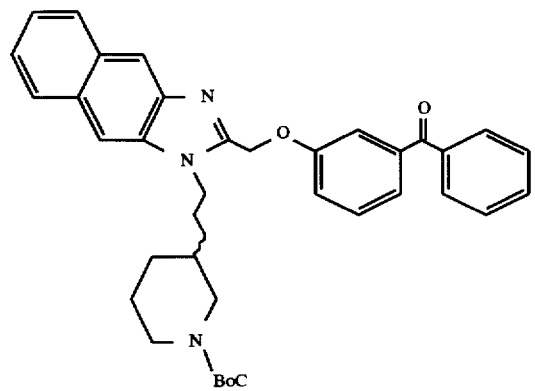

Example 39

Preparation of 2-[3-(but-2-enyl)phenoxymethyl]-1-[3-[1-(t-butoxycarbonyl)piperidin-3-yl]propyl]-1H-naphth[2,3-d]imidazole

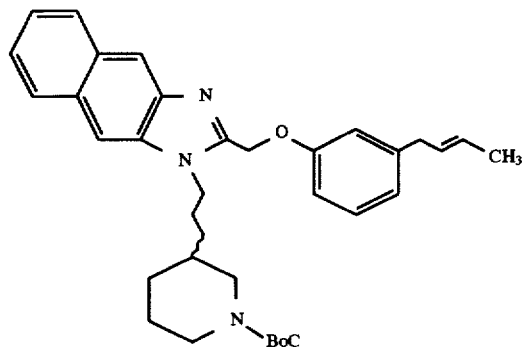

Example 40

Preparation of 2-(3,4,5-trimethoxyphenoxymethyl)-1-[3-[1-(t-butoxycarbonyl)piperidin-3-yl]propyl]-1H-naphth[2,3-d]imidazole

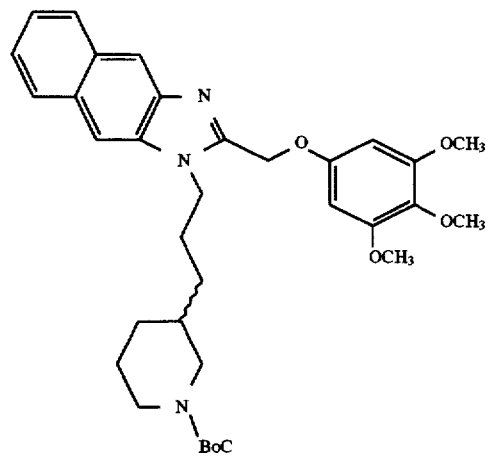

Example 41

Preparation of 2-(4-chlorophenoxymethyl)-1-(3-phenylpropyl)-1H-naphth[2,3-d]imidazole

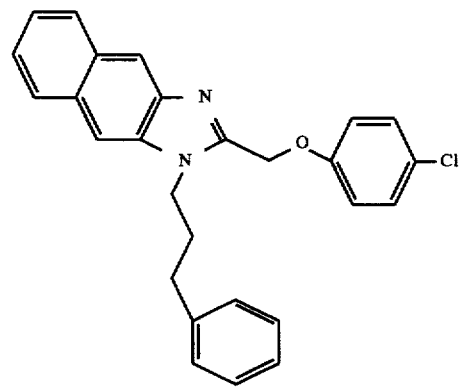

Example 42

Preparation of 2-(4-chlorophenoxymethyl)-1-(3-cyclohexylpropyl)-1H-naphth[2,3-d]imidazole

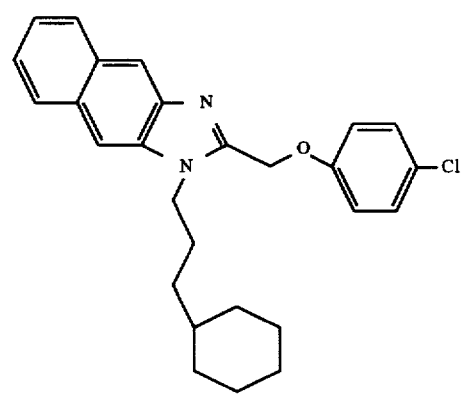

Example 43

Preparation of 2-(4-chlorophenoxymethyl)-1-[3-(pyrid-3-yl)propyl]-1H-naphth[2,3-d]imidazole

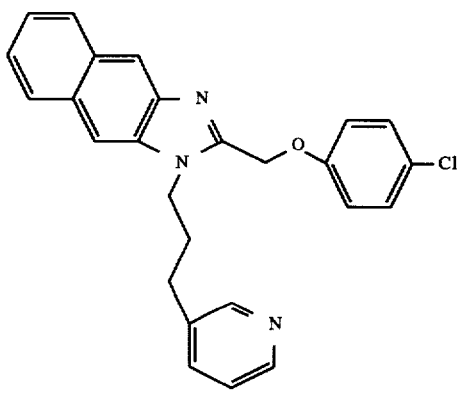

GENERAL PROCEDURE FOR REMOVAL OF THE T-BUTOXYCARBONYL PROTECTING GROUP

Example 44

Preparation of 2-(4-chlorophenoxymethyl)-1-[3-(piperidin-2-yl)propyl]-1H-naphth[2,3-d]imidazole trifluoroacetate salt

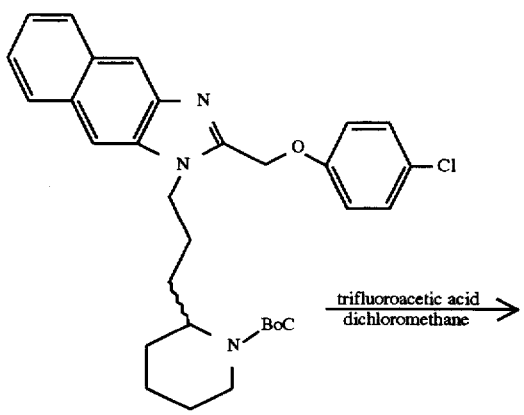

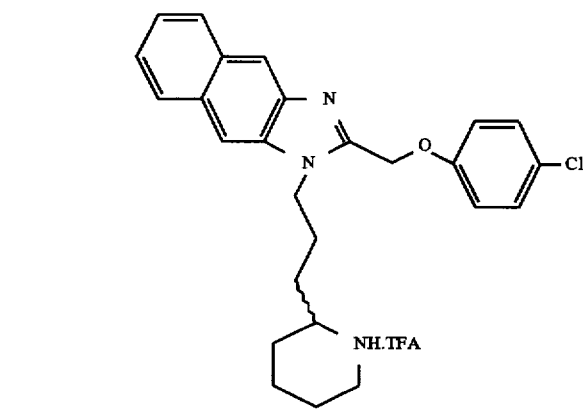

To the amino-protected 1H-naphth[2,3-d]imidazole is added a 1:1 mixture of trifluoroacetic acid in dichloromethane. The resulting mixture is stirred at room temperature for about one hour. The progress of the reaction is monitored by thin layer chromatography. The solvents are removed in vacuo and the residue is triturated with diethyl ether (3×10 ml) and dried under vacuum to yield white crystalline hydroscopic solids.

IR and NMR are consistent with the desired title product. FDMS 433, 434 (M+).

Example 45

Preparation of 2-(4-chlorophenoxymethyl)-1-[3-(piperidin-3-yl)propyl]-1H-naphth[2,3-d]imidazole trifluoroacetate salt

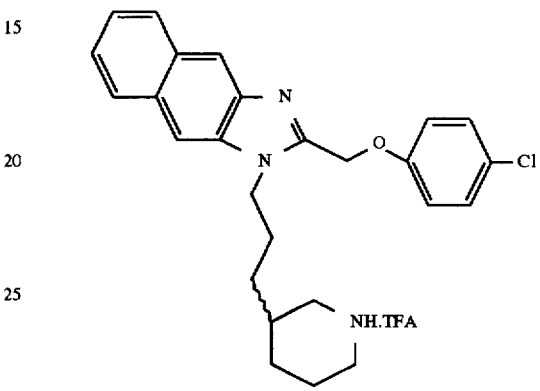

IR and NMR are consistent with the desired title product. FDMS 433, 434 (M+).

Analysis for $C_{26}H_{28}ClN_3O$:

Theory: C, 61.37; H, 5.39; N, 7.67.
Found: C, 60.20; H, 5.42; N, 7.80.

The following compounds are prepared essentially as described above.

Example 46

Preparation of 2-[4-(thiazol-2-yl)benzyloxymethyl]-1-[3-(piperidin-2-yl)propyl]-1H-naphth[2,3-d]imidazole

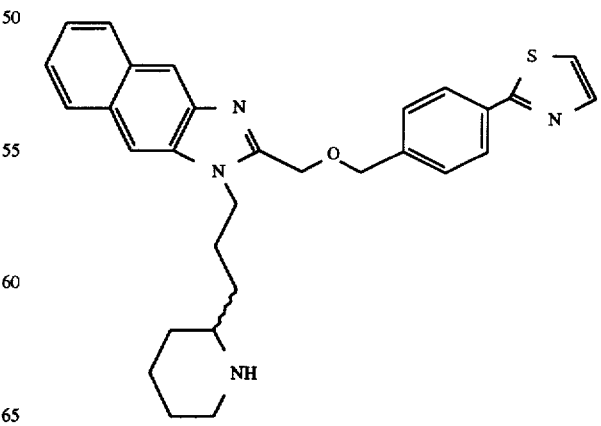

Example 47
Preparation of 2-(4-cyclohexylphenoxymethyl)-1-[3-(piperidin-3-yl)propyl]-1H-naphth[2,3-d]imidazole

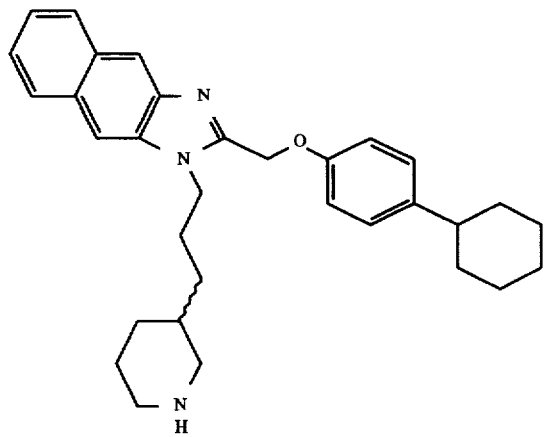

Example 48
Preparation of 2-(3-benzoylphenoxymethyl)-1-[3-(piperidin-3-yl)propyl]-1H-naphth[2,3-d]imidazole

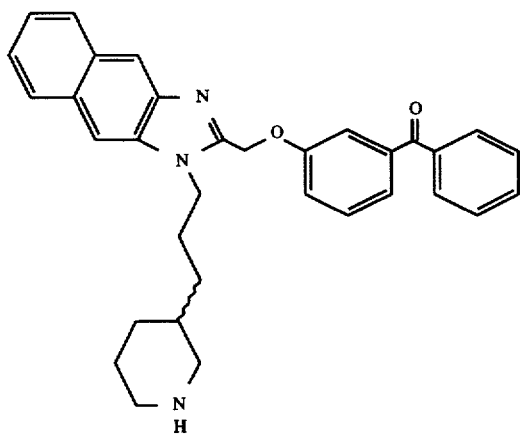

Example 49
Preparation of 2-[3-(but-2-enyl)phenoxymethyl]-1-[3-(piperidin-3-yl)propyl]-1H-naphth[2,3-d]imidazole

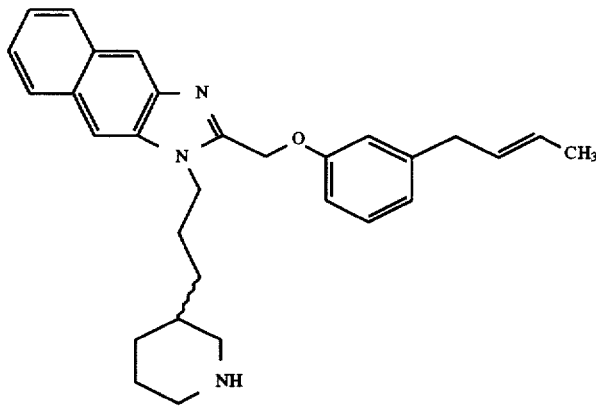

Example 50
Preparation of 2-(3,4,5-trimethoxyphenoxymethyl)-1-[3-(piperidin-3-yl)propyl]-1H-naphth[2,3-d]imidazole

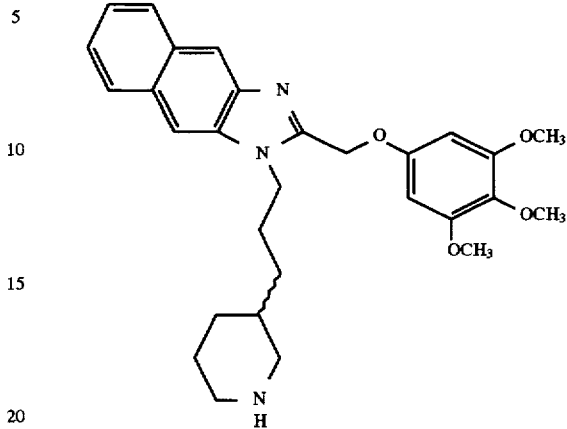

By substantially following the procedures described above one skilled in the art can prepare the other compounds of Formula I.

The compounds of the present invention bind to receptors specific for neuropeptide Y as well as the closely related neuropeptides. [For a review of neuropeptide Y receptors, see, D. Gehlert, *Life Sciences*, 55:551–562 (1994); P. A. Hipskind and D. R. Gehlert, *Annual Reports in Medicinal Chemistry*, 31:1 (1996)]. Receptors for neuropeptide Y and peptide YY have considerable overlap while pancreatic polypeptide appears to have its own distinct set of receptors. Many, but not all, of the effects of neuropeptide Y can be replicated using peptide YY.

Two subtypes of receptors for neuropeptide Y were initially proposed on the basis of the affinity of the 13–36 fragment of neuropeptide Y using a preparation of the sympathetic nervous system. While these are the best established receptors for neuropeptide Y, a substantial body of evidence exists that there are additional receptor subtypes. The best established is a Y-3 receptor that is responsive to neuropeptide Y, but not to peptide YY. Another recently delineated receptor has been described that binds peptide YY with high affinity and neuropeptide Y with lower affinity.

While the pharmacology of the feeding response to neuropeptide Y appears to be Y-1 in nature, a separate "feeding receptor" has been proposed. Several of the receptors have been successfully cloned to date. The following paragraphs summarize the available information on the known neuropeptide Y receptor subtypes and their potential role in physiological function.

Y-1 Receptor

The Y-1 receptor is the best characterized receptor for neuropeptide Y. This receptor is generally considered to be postsynaptic and mediates many of the known actions of neuropeptide Y in the periphery. Originally, this receptor was described as having poor affinity for C-terminal fragments of neuropeptide Y, such as the 13–36 fragment, but interacts with the full length neuropeptide Y and peptide YY with equal affinity. C. Wahlestedt, et al., *Regulatory Peptides*, 13:307–318 (1986); C. Wahlestedt, et al., NEURONAL MESSENGERS IN VASCULAR FUNCTION, 231–241 (Nobin, et al., eds. 1987). Substitution of the amino acid at position 34 with a proline (Pro$^{34}$) results in a protein which is specific for the Y-1 receptor. E. K. Potter, et al., *European Journal of Pharmacology*, 193:15–19 (1991). This tool has been used to establish a role for the Y-1 receptor in a variety of functions. The receptor is thought to be coupled to adenylate cyclase in an inhibitory manner in cerebral cortex, vascular smooth muscle cells, and SK-N-MC cells. [For a review, see, B. J. McDermott, et al., *Cardiovascular Research*, 27:893–905 (1993)]. This action is prevented by application of pertussis toxin confirming the role of a G-protein coupled receptor. The Y-1 receptor mediates the mobilization of intracellular calcium in a porcine vascular smooth muscle cells and human erythroleukemia cells.

The cloned human Y-1 receptor can couple to either phosphotidylinositol hydrolysis or the inhibition of adenylate cyclase, depending on the type of cell in which the receptor is expressed. H. Herzog, et al., *Proceedings of the National Academy of Sciences (USA)*, 89:5794–5798 (1992). The Y-1 receptor has been reported to couple to either second messenger system when studied using tissue preparations or cell lines naturally expressing the receptor. D. Gehlert, supra, at 553. The Y-1 receptor cannot, therefore, be distinguished solely on the basis of coupling to a single second messenger.

Modulation of a Y-1 receptor (either a typical or an atypical Y-1 receptor) is believed to influence multiple physiological conditions, including, but not limited to, obesity or appetite disorder, adult onset diabetes, bulimia nervosa, pheochromocytoma-induced hypertension, subarachnoid hemorrhage, neurogenic vascular hypertrophy, hypertension, anxiety, and anorexia nervosa. PCT Patent Publication WO 96/16542, published Jun. 6, 1996, at page 135, and the references cited therein.

Y-2 Receptor

As with the Y-1 receptor, this receptor subtype was first delineated using vascular preparations. Pharmacologically, the Y-2 receptor is distinguished from Y-1 by exhibiting affinity for C-terminal fragments of neuropeptide Y. The receptor is most often differentiated by the use of neuropeptide Y(13–36), though the 3–36 fragment of neuropeptide Y and peptide YY provides improved affinity and selectivity. Y. Dumont, et al., *Society for Neuroscience Abstracts*, 19:726 (1993). Like Y-1 receptor, this receptor is coupled to the inhibition of adenylate cyclase, though in some preparations it may not be sensitive to pertussis toxin. The Y-2 receptor was found to reduce the intracellular levels of calcium in the synapse by selective inhibition of N-type calcium channels. Like the Y-1 receptor, the Y-2 receptor may exhibit differential coupling to second messengers. The Y2 receptor is believed to be involved in modulating hypertension, epileptic seizure, and neurogenic vascular hypertrophy. PCT Patent Publication WO 96/16542, published Jun. 6, 1996, at page 135, and the references cited therein.

The Y-2 receptors are found in a variety of brain regions, including the hippocampus, substantia nigra-lateralis, thalamus, hypothalamus, and brainstem. In the periphery, Y-2 is found in the peripheral nervous system, such as sympathetic, parasympathetic, and sensory neurons. In all these tissues, Y-2 receptors mediate a decrease in the release of neurotransmitters. The Y-2 receptor has been cloned using expression cloning techniques. P. M. Rose, et al., *Journal of Biological Chemistry*, 270:22661 (1995); C. Gerald, et al., *Journal of Biological Chemistry*, 270:26758 (1995); D. R. Gehlert, et al., *Molecular Pharmacology*, 49:224 (1996).

Y-3 Receptor

This receptor has high affinity for neuropeptide Y while having lower affinity for peptide YY. While neuropeptide Y is a fully efficacious agonist at this receptor population, peptide YY is weakly efficacious. This pharmacological property is used to define this receptor. A receptor that has similar pharmacology to the Y-3 receptor has been identified in the CA3 region of the hippocampus using electrophysiological techniques. This receptor may potentiate the excitatory response of these neurons to N-methyl-D-aspartate (NMDA). F. P. Monnet, et al., *European Journal of Pharmacology*. 182:207–208 (1990). This receptor is believed to modulate hypertension. PCT Patent Publication WO 96/16542, published Jun. 6, 1996, at page 135, and the references cited therein.

The presence of this receptor is best established in the rat brainstem, specifically in the nucleus tractus solitarius. Application of neuropeptide Y to this region produces a dose-dependent reduction in blood pressure and heart rate. This area of the brain also may have significant contributions from the Y-1 and Y-2 receptor. Neuropeptide Y also inhibits the acetylcholine-induced release of catecholamines from the adrenal medulla, presumably through a Y-3 receptor. C. Wahlestedt, et al., *Life Sciences*. 50:PL7–PL14 (1992).

Peptide YY Preferring Receptor

A fourth receptor has been described that exhibits a modest preference for peptide YY over neuropeptide Y. This receptor was first described in the rat small intestine as having a 5–10 fold higher affinity for peptide YY over neuropeptide Y. M. Laburthe, et al., *Endocrinology*, 118:1910–1917 (1986). Subsequently, this receptor was found in the adipocyte and a kidney proximal tubule cell line. This receptor is coupled in an inhibitory manner to adenylate cyclase and is sensitive to pertussis toxin.

In the intestine, this receptor produces a potent inhibition of fluid and electrolyte secretion. The receptor is localized to the crypt cells where intestinal chloride secretion is believed to take place. The peptide YY preferring receptor in adipocytes mediates a reduction in lipolysis by way of a cyclic adenosine monophosphate (cAMP)-dependent mechanism.

"Feeding Receptor"

One of the earliest discovered central effects of neuropeptide Y was a profound increase in food intake that was observed following the hypothalmic administration of the peptide to rats. The response was greatest when the peptide was infused into the perifornical region of the hypothalamus. B. G. Stanley, et al, *Brain Research*, 604:304–317 (1993). While the pharmacology of this response resembled the Y-1 receptor, the 2–36 fragment of neuropeptide Y was significantly more potent than neuropeptide Y. In addition, intracerebroventricular neuropeptide Y(2–36) fully stimulates feeding, but does not reduce body temperature as does full length neuropeptide Y. F. B. Jolicoeur, et al., *Brain Research Bulletin*, 26:309–311 (1991). Two recent patent publications describe the cloning and expression of the Y5 receptor, believed to be the "feeding receptor". Patent Cooperation Treaty Publication WO 96/16542, published Jun. 6, 1996; and Australian Patent Publication AU 956467 A0, published Nov. 30, 1995.

The biological activity of the compounds of the present invention was evaluated employing an initial screening assay which rapidly and accurately measured the binding of the tested compound to known neuropeptide Y receptor sites. Assays useful for evaluating neuropeptide Y receptor antagonists are well known in the art. See, e.g., U.S. Pat. No. 5,284,839, issued Feb. 8, 1994, which is herein incorporated by reference. See also, M. W. Walker, et al., *Journal of Neurosciences*, 8:2438–2446 (1988).

Neuropeptide Y Binding Assay

The ability of the compounds of the instant invention were assessed as to their ability to bind to neuropeptide Y using a protocol essentially as described in M. W. Walker, et al., supra. In this assay the cell line SK-N-MC was employed. This cell line was received from Sloane-Kettering Memorial Hospital, New York. These cells were cultured in T-150 flasks using Dulbecco's Minimal Essential Media (DMEM) supplemented with 5% fetal calf serum. The cells were manually removed from the flasks by scraping, pelleted, and stored at −70° C.

The pellets were resuspended using a glass homogenizer in 25 mM HEPES (pH 7.4) buffer containing 2.5 mM calcium chloride, 1 mM magnesium chloride, and 2 g/L bacitracin. Incubations were performed in a final volume of 200 μl containing 0.1 nM $^{125}$I-peptide YY (2200 Ci/mmol) and 0.2–0.4 mg protein for about two hours at room temperature.

Nonspecific binding was defined as the amount of radioactivity remaining bound to the tissue after incubating in the presence of 1 μM neuropeptide Y. In some experiments various concentrations of compounds were included in the incubation mixture.

Incubations were terminated by rapid filtration through glass fiber filters which had been presoaked in 0.3% polyethyleneimine using a 96-well harvester. The filters were washed with 5 ml of 50 mM Tris (pH 7.4) at 4° C. and rapidly dried at 60° C. The filters were then treated with melt-on scintillation sheets and the radioactivity retained on the filters were counted. The results were analyzed using various software packages. Protein concentrations were measured using standard coumassie protein assay reagents using bovine serum albumin as standards.

Many of the compounds prepared supra showed significant activity as neuropeptide Y receptor antagonists ($K_i$=10 μM to 0.1 nM). As the compounds of Formula I are effective neuropeptide Y receptor antagonists, these compounds are of value in the treatment of a wide variety of clinical conditions which are characterized by the presence of an excess of neuropeptide Y. Thus, the invention provides methods for the treatment or prevention of a physiological disorder associated with an excess of neuropeptide Y, which method comprises administering to a mammal in need of said treatment an effective amount of a compound of Formula I or a pharmaceutically acceptable salt, solvate or prodrug thereof. The term "physiological disorder associated with an excess of neuropeptide Y" encompasses those disorders associated with an inappropriate stimulation of neuropeptide Y receptors, regardless of the actual amount of neuropeptide Y present in the locale.

These physiological disorders include:

disorders or diseases pertaining to the heart, blood vessels or the renal system, such as vasospasm, heart failure, shock, cardiac hypertrophy, increased blood pressure, angina, myocardial infarction, sudden cardiac death, congestive heart failure, arrythmia, peripheral vascular disease, and abnormal renal conditions such as impaired flow of fluid, abnormal mass transport, or renal failure;

conditions related to increased sympathetic nerve activity for example, during or after coronary artery surgery, and operations and surgery in the gastrointestinal tract;

cerebral diseases and diseases related to the central nervous system, such as cerebral infarction, neurodegeneration, epilepsy, stroke, and conditions related to stroke, cerebral vasospasm and hemorrhage, depression, anxiety, schizophrenia, dementia, seizure, and epilepsy;

conditions related to pain or nociception;

diseases related to abnormal gastrointestinal motility and secretion, such as different forms of ileus, urinary incontinence, and Crohn's disease;

abnormal drink and food intake disorders, such as obesity, anorexia, bulimia, and metabolic disorders;

diseases related to sexual dysfunction and reproductive disorders;

conditions or disorders associated with inflammation;

respiratory diseases, such as asthma and conditions related to asthma and bronchoconstriction; and diseases related to abnormal hormone release, such as leutinizing hormone, growth hormone, insulin, and prolactin.

The compounds of Formula I are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

The present invention also includes methods employing pharmaceutical compositions which contain, as the active ingredient, a compound of Formula I associated with pharmaceutically acceptable carriers. In making the compositions of the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage form" refers to physically discrete units suitable as unitary dosages dosages for human subjects and other mammals, each unit containing a predetermined quantity of active material calculated to produce the desired therapeutic effect, in association with a suitable pharmaceutical excipient.

The active compound is effective over a wide dosage range. For examples, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid compositions such as tablets the principal active ingredient is mixed with a pharmaceutical excipient to form a solid preformulation composition containing a homogeneous mixture of a compound of the present invention. When referring to these preformulation compositions as homogeneous, it is meant that the active ingredient is dipsersed evenly throughout the composition so that the composition may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face mask, tent, or intermittent positive pressure breathing machine. Solution, suspension, or powder compsoitions may be administered, preferably orally or nasally, from devices which deliver the formulation in an appropriate manner.

The following examples illustrate the pharmaceutical compositions of the present invention.

FORMULATION PREPARATION 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION PREPARATION 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION PREPARATION 3

A dry powder inhaler formulation is prepared containing the following components:

| Ingredient | Weight % |
|---|---|
| Active Ingredient | 5 |
| Lactose | 95 |

The active mixture is mixed with the lactose and the mixture is added to a dry powder inhaling appliance.

FORMULATION PREPARATION 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION PREPARATION 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION PREPARATION 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION PREPARATION 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION PREPARATION 8

Capsules, each containing 15 mg of medicament, are made as follows:

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION PREPARATION 9

An intravenous formulation may be prepared as follows:

| Ingredient | Quantity |
| --- | --- |
| Active Ingredient | 250.0 mg |
| Isotonic saline | 1000 ml |

FORMULATION PREPARATION 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid praffin and emulsifying wax are incorporated and stirred until dissolved. The active ingredient is added and stirring is continued until dispersed. The mixture is then cooled until solid.

FORMULATION PREPARATION 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

We claim:

1. A method of treating a physiological disorder associated with an excess of neuropeptide Y, which method comprises administering to a mammal in need of said treatment an effective amount of a compound of the formula

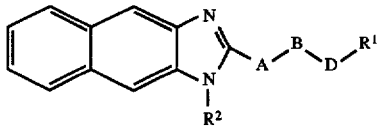

wherein:

A is $C_1$–$C_6$ alkylenyl;

B is —O—, —NH—, or —S—;

D is a bond or $C_1$–$C_6$ alkylenyl;

$R^1$ is $C_3$–$C_8$ cycloalkyl, $C_3$–$C_8$ cycloalkenyl, phenyl, phenoxy, naphthyl, or naphthyloxy, any one of which phenyl, $C_3$–$C_8$ cycloalkyl, phenoxy, naphthyl, or naphthyloxy moieties may be substituted with one or more moieties selected from the group consisting of halo, trifluoromethyl, $C_1$–$C_6$ alkyl, $C_2$–$C_7$ alkenyl, $C_2$–$C_7$ alkynyl, $C_1$–$C_6$ alkoxy, $C_1$–$C_6$ alkylthio, $C_1$–$C_6$ alkylamino, $C_2$–$C_7$ alkanoyl, hydroxy, heterocyclic, unsaturated heterocyclic, $C_3$–$C_8$ cycloalkyl, $C_3$–$C_8$ cycloalkenyl, phenyl, phenoxy, benzyl, benzyloxy, and benzoyl;

$R^2$ is $C_1$–$C_{12}$ alkyl, $C_2$–$C_7$ alkenyl, $C_2$–$C_7$ alkynyl, heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)-, which $C_1$–$C_{12}$ alkyl, $C_2$–$C_7$ alkenyl, or $C_2$–$C_7$ alkynyl may be substituted with halo or hydroxy, and any one of which heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl ($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)- groups may be substituted with one or more moieties selected from the group consisting of $C_1$–$C_6$ alkyl, hydroxy, $C_1$–$C_6$ alkoxy, phenyl, naphthyl, phenyl($C_1$–$C_6$ alkylenyl)-, naphthyl ($C_1$–$C_6$ alkylenyl)-, halo, trifluoromethyl, $C_2$–$C_7$ alkenyl, $C_2$–$C_7$ alkynyl, $C_1$–$C_6$ alkoxy, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, $C_1$–$C_6$ alkylthio, amino, nitro, and an amino-protecting group;

or a pharmaceutically acceptable salt or solvate thereof.

2. A method as claimed in claim 1 wherein A is methylene, or a pharmaceutically acceptable salt or solvate thereof.

3. A method as claimed in claim 2 wherein B is —O—, or a pharmaceutically acceptable salt or solvate thereof.

4. A method as claimed in claim 3 wherein D is a bond or methylene, or a pharmaceutically acceptable salt or solvate thereof.

5. A method as claimed in claim 4 wherein $R^1$ is phenyl or substituted phenyl, or a pharmaceutically acceptable salt or solvate thereof.

6. A method as claimed in claim 5 wherein $R^1$ is phenyl substituted with one or more moieties selected from the group consisting of chloro, fluoro, bromo, methyl, methoxy, trifluoromethyl, ethyl, ethoxy, and acetyl, or a pharmaceutically acceptable salt or solvate thereof.

7. A method as claimed in claim 6 wherein $R^1$ is 4-chlorophenyl, 4-methylphenyl, 4-methoxyphenyl, 3,4,5-trimethoxyphenyl, or 4-acetylphenyl, or a pharmaceutically acceptable salt or solvate thereof.

8. A method as claimed in claim 1 wherein $R^2$ is $C_1$–$C_{12}$ alkyl or heterocyclic($C_1$–$C_6$ alkylenyl)-, or a substituted derivative thereof, or a pharmaceutically acceptable salt or solvate thereof.

9. A method as claimed in claim 8 wherein $R^2$ is hydroxy ($C_1$–$C_4$ alkylenyl)-, halo($C_1$–$C_4$ alkylenyl)-, piperidinyl ($C_1$–$C_4$ alkylenyl)-, pyrrolidinyl($C_1$–$C_4$ alkylenyl)-, or morpholinyl($C_1$–$C_4$ alkylenyl)-, or a substituted derivative thereof, or a pharmaceutically acceptable salt or solvate thereof.

10. A method as claimed in claim 9 wherein the piperidinyl or pyrroldinyl group is substituted with t-butoxycarbonyl or trityl, or a pharmaceutically acceptable salt or solvate thereof.

11. A compound of the formula

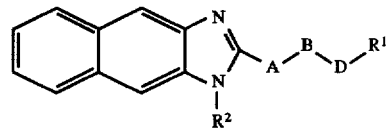

wherein:

A is $C_1$–$C_6$ alkylenyl;

B is —O—, —NH—, or —S—;

D is a bond or $C_1$–$C_6$ alkylenyl;

$R^1$ is $C_3$–$C_8$ cycloalkyl, $C_3$–$C_8$ cycloalkenyl, phenyl, phenoxy, naphthyl, or naphthyloxy, any one of which phenyl, $C_3$–$C_8$ cycloalkyl, phenoxy, naphthyl, or naphthyloxy moieties may be substituted with one or more moieties selected from the group consisting of halo, trifluoromethyl, $C_1$–$C_6$ alkyl, $C_2$–$C_7$ alkenyl, $C_2$–$C_7$ alkynyl, $C_1$–$C_6$ alkoxy, $C_1$–$C_6$ alkylthio, $C_1$–$C_6$ alkylamino, $C_2$–$C_7$ alkanoyl, hydroxy, heterocyclic, unsaturated heterocyclic, $C_3$–$C_8$ cycloalkyl, $C_3$–$C_8$ cycloalkenyl, phenyl, phenoxy, benzyl, benzyloxy, and benzoyl;

$R^2$ is $C_1$–$C_{12}$ alkyl, $C_2$–$C_7$ alkenyl, $C_2$–$C_7$ alkynyl, heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)-, which $C_1$–$C_{12}$ alkyl, $C_2$–$C_7$ alkenyl, or $C_2$–$C_7$ alkynyl may be substituted with halo or hydroxy, and any one of which heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl ($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)- groups may be substituted with one or more moieties selected from the group consisting of $C_1$–$C_6$ alkyl, hydroxy, $C_1$–$C_6$ alkoxy, phenyl, naphthyl, phenyl($C_1$–$C_6$ alkylenyl)-, naphthyl ($C_1$–$C_6$ alkylenyl)-, halo, trifluoromethyl, $C_2$–$C_7$ alkenyl, $C_2$–$C_7$ alkynyl, $C_1$–$C_6$ alkoxy, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, $C_1$–$C_6$ alkylthio, amino, nitro, and an amino-protecting group;

or a salt or solvate thereof.

12. A compound as claimed in claim 11 wherein A is methylene, or a salt or solvate thereof.

13. A compound as claimed in claim 12 wherein B is —O—, or a salt or solvate thereof.

14. A compound as claimed in claim 13 wherein D is a bond or methylene, or a salt or solvate thereof.

15. A compound as claimed in claim 14 wherein $R^1$ is phenyl or substituted phenyl, or a salt or solvate thereof.

16. A compound as claimed in claim 15 wherein $R^1$ is phenyl substituted with one or more moieties selected from the group consisting of chloro, fluoro, bromo, methyl, methoxy, trifluoromethyl, ethyl, ethoxy, and acetyl, or a salt or solvate thereof.

17. A compound as claimed in claim 16 wherein $R^1$ is 4-chlorophenyl, 4-methylphenyl, 4-methoxyphenyl, 3,4,5-trimethoxyphenyl, or 4-acetylphenyl, or a salt or solvate thereof.

18. A compound as claimed in claim 11 wherein $R^2$ is $C_1$–$C_{12}$ alkyl or heterocyclic($C_1$–$C_6$ alkylenyl)-, or a substituted derivative thereof, or a salt or solvate thereof.

19. A compound as claimed in claim 18 wherein $R^2$ is hydroxy($C_1$–$C_4$ alkylenyl)-, halo($C_1$–$C_4$ alkylenyl)-, piperidinyl($C_1$–$C_4$ alkylenyl)-, pyrrolidinyl($C_1$–$C_4$ alkylenyl)-, or morpholinyl($C_1$–$C_4$ alkylenyl)-, or a substituted derivative thereof, or a salt or solvate thereof.

20. A compound as claimed in claim 19 wherein the piperidinyl or pyrroldinyl group is substituted with t-butoxycarbonyl or trityl, or a salt or solvate thereof.

21. A pharmaceutical formulation which comprised a compound of the formula

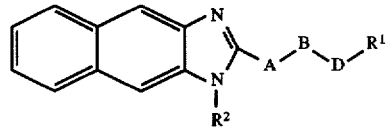

wherein:

A is $C_1$–$C_6$ alkylenyl;

B is —O—, —NH—, or —S—;

D is a bond or $C_1$–$C_6$ alkylenyl;

$R^1$ is $C_3$–$C_8$ cycloalkyl, $C_3$–$C_8$ cycloalkenyl, phenyl, phenoxy, naphthyl, or naphthyloxy, any one of which phenyl, $C_3$–$C_8$ cycloalkyl, phenoxy, naphthyl, or naphthyloxy moieties may be substituted with one or more moieties selected from the group consisting of halo, trifluoromethyl, $C_1$–$C_6$ alkyl, $C_2$–$C_7$ alkenyl, $C_2$–$C_7$ alkynyl, $C_1$–$C_6$ alkoxy, $C_1$–$C_6$ alkylthio, $C_1$–$C_6$ alkylamino, $C_2$–$C_7$ alkanoyl, hydroxy, heterocyclic, unsaturated heterocyclic, $C_3$–$C_8$ cycloalkyl, $C_3$–$C_8$ cycloalkenyl, phenyl, phenoxy, benzyl, benzyloxy, and benzoyl;

$R^2$ is $C_1$–$C_{12}$ alkyl, $C_2$–$C_7$ alkenyl, $C_2$–$C_7$ alkynyl, heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)-, which $C_1$–$C_{12}$ alkyl, $C_2$–$C_7$ alkenyl, or $C_2$–$C_7$ alkynyl may be substituted with halo or hydroxy, and any one of which heterocyclic($C_1$–$C_6$ alkylenyl)-, $C_3$–$C_8$ cycloalkyl, $C_3$–$C_8$ cycloalkenyl, unsaturated heterocyclic($C_1$–$C_6$ alkylenyl)-, phenyl, phenyl ($C_1$–$C_6$ alkylenyl)-, naphthyl, naphthyl($C_1$–$C_6$ alkylenyl)-, phenoxy($C_1$–$C_6$ alkylenyl)-, naphthyloxy($C_1$–$C_6$ alkylenyl)-, or benzoyl($C_1$–$C_6$ alkylenyl)- groups may be substituted with one or more moieties selected from the group consisting of $C_1$–$C_6$ alkyl, hydroxy, $C_1$–$C_6$ alkoxy, phenyl, naphthyl, phenyl($C_1$–$C_6$ alkylenyl)-, naphthyl ($C_1$–$C_6$ alkylenyl)-, halo, trifluoromethyl, $C_2$–$C_7$ alkenyl, $C_2$–$C_7$ alkynyl, $C_1$–$C_6$ alkoxy, heterocyclic, unsaturated heterocyclic, heterocyclic($C_1$–$C_6$ alkylenyl)-, unsaturated heterocyclic($C_1$–$C_6$ alkylenyl)-, heterocyclic($C_1$–$C_6$ alkoxy)-, unsaturated heterocyclic($C_1$–$C_6$ alkoxy)-, $C_3$–$C_8$ cycloalkyl, $C_3$–$C_8$ cycloalkenyl, $C_2$–$C_7$ alkanoyl, $C_2$–$C_7$ alkanoyloxy, $C_1$–$C_6$ alkylamino, $C_1$–$C_6$ alkylthio, amino, nitro, and an amino-protecting group;

or a pharmaceutically acceptable salt or solvate thereof, in combination with one or more pharmaceutically acceptable carriers, excipients, or diluents therefor.

22. A formulation as claimed in claim 21 wherein A is methylene, or a pharmaceutically acceptable salt or solvate thereof.

23. A formulation as claimed in claim 22 wherein B is —O—, or a pharmaceutically acceptable salt or solvate thereof.

24. A formulation as claimed in claim 23 wherein D is a bond or methylene, or a pharmaceutically acceptable salt or solvate thereof.

25. A formulation as claimed in claim 24 wherein $R^1$ is phenyl or substituted phenyl, or a pharmaceutically acceptable salt or solvate thereof.

26. A formulation as claimed in claim 25 wherein $R^1$ is phenyl substituted with one or more moieties selected from the group consisting of chloro, fluoro, bromo, methyl, methoxy, trifluoromethyl, ethyl, ethoxy, and acetyl, or a pharmaceutically acceptable salt or solvate thereof.

27. A formulation as claimed in claim 26 wherein $R^1$ is 4-chlorophenyl, 4-methylphenyl, 4-methoxyphenyl, 3,4,5-trimethoxyphenyl, or 4-acetylphenyl, or a pharmaceutically acceptable salt or solvate thereof.

28. A formulation as claimed in claim 21 wherein $R^2$ is $C_1-C_{12}$ alkyl or heterocyclic($C_1-C_6$ alkylenyl)-, or a substituted derivative thereof, or a pharmaceutically acceptable salt or solvate thereof.

29. A formulation as claimed in claim 28 wherein $R^2$ is hydroxy($C_1-C_4$ alkylenyl)-, halo($C_1-C_4$ alkylenyl)-, piperidinyl($C_1-C_4$ alkylenyl)-, pyrrolidinyl($C_1-C_4$ alkylenyl)-, or morpholinyl($C_1-C_4$ alkylenyl)-, or a substituted derivative thereof, or a pharmaceutically acceptable salt or solvate thereof.

30. A formulation as claimed in claim 29 wherein the piperidinyl or pyrroldinyl group is substituted with t-butoxycarbonyl or trityl, or a pharmaceutically acceptable salt or solvate thereof.

* * * * *